United States Patent
Leuschner et al.

(10) Patent No.: US 11,066,693 B2
(45) Date of Patent: *Jul. 20, 2021

(54) METHODS FOR DIAGNOSING LHRH OR HCG/LH RECEPTOR EXPRESSING TUMORS, CANCERS AND NEOPLASIAS

(71) Applicant: ESPERANCE PHARMACEUTICALS, INC., Houston, TX (US)

(72) Inventors: Carola Leuschner, Houston, TX (US); Hector Alila, Katy, TX (US)

(73) Assignee: ESPERANCE PHARMACEUTICALS, INC., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/154,486

(22) Filed: Oct. 8, 2018

(65) Prior Publication Data

US 2019/0040450 A1 Feb. 7, 2019

Related U.S. Application Data

(63) Continuation of application No. 12/975,058, filed on Dec. 21, 2010, now Pat. No. 10,093,961.

(60) Provisional application No. 61/289,010, filed on Dec. 22, 2009.

(51) Int. Cl.
*G01N 33/53* (2006.01)
*G01N 33/566* (2006.01)
*G01N 33/574* (2006.01)
*C12Q 1/68* (2018.01)

(52) U.S. Cl.
CPC .............. *C12Q 1/68* (2013.01); *G01N 33/53* (2013.01); *G01N 33/566* (2013.01); *G01N 33/574* (2013.01)

(58) Field of Classification Search
None
See application file for complete search history.

(56) References Cited

U.S. PATENT DOCUMENTS

| 2003/0166503 A1 | 9/2003 | Van Groeninghen |
| 2006/0247177 A1 | 11/2006 | Millar |
| 2009/0269341 A1 | 10/2009 | Leuschner et al. |

FOREIGN PATENT DOCUMENTS

WO  WO 2009/094634  * 7/2009 ............. A61P 35/00

OTHER PUBLICATIONS

Keller et al., Cancer Res 2005; 65: (13): 5857-5863 (Year: 2005).*
Keller, G. et al., Human Malignant Melanomas Express Receptors for Luteinizing Hormone Releasing Hormone Allowing Targeted Therapy with Cytotoxic Luteinizing Hormone Releasing Hormone Analogue, Cancer Res, 2005, 65(13):5837-5863.
Treszl, A., et al., Substantial Expression of Luteinizing Hormone-Releasing Hormone (LHRH) Receptor Type I in Human Uveal Melanoma, oNCOTARGET, 2013, 4:1721-1728.
Leuschner et al., MGR Annual Meeting; Abstract #4666: "Targeted oncolytic peptide for treatment of ovarian cancers", Apr. 18-22, 2009; Denver, CO; published May 2009. (Year: 2009).
Christodoulou et al., British Journal of Cancer, 1998; 77: 2088-2097. (Year: 1998).
Chien et al., Int. J. Gynecol Cancer, 2004; 14: 451-458.
Schally, Life Sciences, 2003; 72: 2305-2320.
Stangelberger et al., The Prostate, 2006; 66: 200-210.
Rajaniemi et al., Acta Obstet Gynecol Scand Suppl, 1981; 101: 83-86.
Kahan et al., Cancer, 1999; 85: 2608-2615.
Ben-Yehudah et al., Expert Rev Anticancer Ther, 2004; 4: 151-161.
Keller et al., European Journal of Cancer, 2005; 41: 2196-2202.
Emerson et al., Am J Clin Pathol 2006; 125: 176-183.
Volker et al., Am J Obstet Gynecol, 2002; 186: 171-179.
Phillips, A., J Pharm Pharmacology, 2001; 53: 1169-1174.
Vidal et al., European Journal of Cancer, 2005; 41: 2812-2818.
Pirollo et al., Cancer Res. 2008; 68(5): 1247-1250.
Schally and Nagy (Trends Endocrinol Metab, 2004; 15: 300-310.

* cited by examiner

*Primary Examiner* — Christina M Borgeest
(74) *Attorney, Agent, or Firm* — Pillsbury Winthrop Shaw Pittman LLP

(57) ABSTRACT

The invention relates to diagnosis, detection, screening, identifying and predicting methods. In various embodiments, methods of the invention include diagnosis, detection, or screening for a hyperproliferative disorder (e.g., a tumor, cancer or neoplasia) in the subject; identifying a subject that will or is likely to respond to a therapy for a hyperproliferative disorder (e.g., a tumor, cancer or neoplasia); and predicting therapeutic efficacy of a hyperproliferative disorder (e.g., a tumor, cancer or neoplasia) treatment in a subject.

18 Claims, 2 Drawing Sheets

Specification includes a Sequence Listing.

SEQUENCE LISTING

<160> NUMBER OF SEQ ID NOS: 9

<210> SEQ ID NO 1
<211> LENGTH: 28
<212> TYPE: PRT
<213> ORGANISM: Homo sapiens

<400> SEQUENCE: 1

Lys Phe Ala Lys Phe Ala Lys Phe Ala Lys Phe Ala Lys Lys Phe
1               5                   10                  15

Ala Lys Gln His Trp Ser Tyr Gly Leu Arg Pro Gly
            20                  25

<210> SEQ ID NO 2
<211> LENGTH: 328
<212> TYPE: PRT
<213> ORGANISM: Homo sapiens

<400> SEQUENCE: 2

Met Ala Asn Ser Ala Ser Pro Glu Gln Asn Gln His Cys Ser Ala
1               5                   10                  15

Ile Asn Asn Ser Ile Pro Leu Met Gln Gly Asn Leu Pro Thr Leu Thr
                20                  25                  30

Leu Ser Gly Lys Ile Arg Val Thr Val Thr Phe Phe Leu Phe Leu Leu
                35                  40                  45

Ser Ala Thr Phe Asn Ala Ser Phe Leu Leu Lys Leu Gln Lys Trp Thr
50                  55                  60

Gln Lys Lys Glu Lys Gly Lys Lys Leu Ser Arg Met Lys Leu Leu Leu
65                  70                  75                  80

Lys His Leu Thr Leu Ala Asn Leu Leu Glu Thr Leu Ile Val Met Pro
                85                  90                  95

Leu Asp Gly Met Trp Asn Ile Thr Val Gln Trp Tyr Ala Gly Glu Leu
                100                 105                 110

Leu Cys Lys Val Leu Ser Tyr Leu Lys Leu Phe Ser Met Tyr Ala Pro
                115                 120                 125

Ala Phe Met Met Val Val Ile Ser Leu Asp Arg Ser Leu Ala Ile Thr
                130                 135                 140

Arg Pro Leu Ala Leu Lys Ser Asn Ser Lys Val Gly Gln Ser Met Val
145                 150                 155                 160

Gly Leu Ala Trp Ile Leu Ser Ser Val Phe Ala Gly Pro Gln Leu Tyr
                165                 170                 175

Ile Phe Arg Met Ile His Leu Ala Asp Ser Ser Gly Gln Thr Lys Val
                180                 185                 190

Phe Ser Gln Cys Val Thr His Cys Ser Phe Ser Gln Trp Trp His Gln
                195                 200                 205

Ala Phe Tyr Asn Phe Phe Thr Phe Ser Cys Leu Phe Ile Ile Pro Leu
                210                 215                 220

Phe Ile Met Leu Ile Cys Asn Ala Lys Ile Ile Phe Thr Leu Thr Arg
225                 230                 235                 240

Val Leu His Gln Asp Pro His Glu Leu Gln Leu Asn Gln Ser Lys Asn
                245                 250                 255

Asn Ile Pro Arg Ala Arg Leu Lys Thr Leu Lys Met Thr Val Ala Phe
                260                 265                 270

Ala Thr Ser Phe Thr Val Cys Trp Thr Pro Tyr Tyr Val Leu Gly Ile
                275                 280                 285

Trp Tyr Trp Phe Asp Pro Glu Met Leu Asn Arg Leu Ser Asp Pro Val

```
              290                 295                 300
Asn His Phe Phe Phe Leu Phe Ala Phe Leu Asn Pro Cys Phe Asp Pro
305                 310                 315                 320

Leu Ile Tyr Gly Tyr Phe Ser Leu
                325
```

<210> SEQ ID NO 3
<211> LENGTH: 699
<212> TYPE: PRT
<213> ORGANISM: Homo sapiens
<400> SEQUENCE: 3

```
Met Lys Gln Arg Phe Ser Ala Leu Gln Leu Leu Lys Leu Leu Leu Leu
1               5                   10                  15

Leu Gln Pro Pro Leu Pro Arg Ala Leu Arg Glu Ala Leu Cys Pro Glu
                20                  25                  30

Pro Cys Asn Cys Val Pro Asp Gly Ala Leu Arg Cys Pro Gly Pro Thr
            35                  40                  45

Ala Gly Leu Thr Arg Leu Ser Leu Ala Tyr Leu Pro Val Lys Val Ile
        50                  55                  60

Pro Ser Gln Ala Phe Arg Gly Leu Asn Glu Val Ile Lys Ile Glu Ile
65                  70                  75                  80

Ser Gln Ile Asp Ser Leu Glu Arg Ile Glu Ala Asn Ala Phe Asp Asn
                85                  90                  95

Leu Leu Asn Leu Ser Glu Ile Leu Ile Gln Asn Thr Lys Asn Leu Arg
            100                 105                 110

Tyr Ile Glu Pro Gly Ala Phe Ile Asn Leu Pro Arg Leu Lys Tyr Leu
        115                 120                 125

Ser Ile Cys Asn Thr Gly Ile Arg Lys Phe Pro Asp Val Thr Lys Val
130                 135                 140

Phe Ser Ser Glu Ser Asn Phe Ile Leu Glu Ile Cys Asp Asn Leu His
145                 150                 155                 160

Ile Thr Thr Ile Pro Gly Asn Ala Phe Gln Gly Met Asn Asn Glu Ser
                165                 170                 175

Val Thr Leu Lys Leu Tyr Gly Asn Gly Phe Glu Glu Val Gln Ser His
            180                 185                 190

Ala Phe Asn Gly Thr Thr Leu Thr Ser Leu Glu Leu Lys Glu Asn Val
        195                 200                 205

His Leu Glu Lys Met His Asn Gly Ala Phe Arg Gly Ala Thr Gly Pro
    210                 215                 220

Lys Thr Leu Asp Ile Ser Ser Thr Lys Leu Gln Ala Leu Pro Ser Tyr
225                 230                 235                 240

Gly Leu Glu Ser Ile Gln Arg Leu Ile Ala Thr Ser Ser Tyr Ser Leu
                245                 250                 255

Lys Lys Leu Pro Ser Arg Glu Thr Phe Val Asn Leu Leu Glu Ala Thr
            260                 265                 270

Leu Thr Tyr Pro Ser His Cys Cys Ala Phe Arg Asn Leu Pro Thr Lys
        275                 280                 285

Glu Gln Asn Phe Ser His Ser Ile Ser Glu Asn Phe Ser Lys Gln Cys
    290                 295                 300

Glu Ser Thr Val Arg Lys Val Ser Asn Lys Thr Leu Tyr Ser Ser Met
305                 310                 315                 320

Leu Ala Glu Ser Glu Leu Ser Gly Trp Asp Tyr Glu Tyr Gly Phe Cys
                325                 330                 335
```

```
Leu Pro Lys Thr Pro Arg Cys Ala Pro Glu Pro Asp Ala Phe Asn Pro
            340                 345                 350

Cys Glu Asp Ile Met Gly Tyr Asp Phe Leu Arg Val Leu Ile Trp Leu
            355                 360                 365

Ile Asn Ile Leu Ala Ile Met Gly Asn Met Thr Val Leu Phe Val Leu
        370                 375                 380

Leu Thr Ser Arg Tyr Lys Leu Thr Val Pro Arg Phe Leu Met Cys Asn
385                 390                 395                 400

Leu Ser Phe Ala Asp Phe Cys Met Gly Leu Tyr Leu Leu Leu Ile Ala
                405                 410                 415

Ser Val Asp Ser Gln Thr Lys Gly Gln Tyr Tyr Asn His Ala Ile Asp
            420                 425                 430

Trp Gln Thr Gly Ser Gly Cys Ser Thr Ala Gly Phe Phe Thr Val Phe
            435                 440                 445

Ala Ser Glu Leu Ser Val Tyr Thr Leu Thr Val Ile Thr Leu Glu Arg
        450                 455                 460

Trp His Thr Ile Thr Tyr Ala Ile His Leu Asp Gln Lys Leu Arg Leu
465                 470                 475                 480

Arg His Ala Ile Leu Ile Met Leu Gly Gly Trp Leu Phe Ser Ser Leu
                485                 490                 495

Ile Ala Met Leu Pro Leu Val Gly Val Ser Asn Tyr Met Lys Val Ser
            500                 505                 510

Ile Cys Phe Pro Met Asp Val Glu Thr Thr Leu Ser Gln Val Tyr Ile
            515                 520                 525

Leu Thr Ile Leu Ile Leu Asn Val Val Ala Phe Phe Ile Ile Cys Ala
530                 535                 540

Cys Tyr Ile Lys Ile Tyr Phe Ala Val Arg Asn Pro Glu Leu Met Ala
545                 550                 555                 560

Thr Asn Lys Asp Thr Lys Ile Ala Lys Lys Met Ala Ile Leu Ile Phe
                565                 570                 575

Thr Asp Phe Thr Cys Met Ala Pro Ile Ser Phe Phe Ala Ile Ser Ala
            580                 585                 590

Ala Phe Lys Val Pro Leu Ile Thr Val Thr Asn Ser Lys Val Leu Leu
            595                 600                 605

Val Leu Phe Tyr Pro Ile Asn Ser Cys Ala Asn Pro Phe Leu Tyr Ala
            610                 615                 620

Ile Phe Thr Lys Thr Phe Gln Arg Asp Phe Phe Leu Leu Leu Ser Lys
625                 630                 635                 640

Phe Gly Cys Cys Lys Arg Arg Ala Glu Leu Tyr Arg Arg Lys Asp Phe
                645                 650                 655

Ser Ala Tyr Thr Ser Asn Cys Lys Asn Gly Phe Thr Gly Ser Asn Lys
            660                 665                 670

Pro Ser Gln Ser Thr Leu Lys Leu Ser Thr Leu His Cys Gln Gly Thr
            675                 680                 685

Ala Leu Leu Asp Lys Thr Arg Tyr Thr Glu Cys
            690                 695

<210> SEQ ID NO 4
<211> LENGTH: 10
<212> TYPE: PRT
<213> ORGANISM: Homo sapiens

<400> SEQUENCE: 4

Glu His Trp Ser Tyr Gly Leu Arg Pro Gly
1               5                   10
```

<210> SEQ ID NO 5
<211> LENGTH: 10
<212> TYPE: PRT
<213> ORGANISM: Homo sapiens

<400> SEQUENCE: 5

Glu His Trp Ser His Gly Trp Tyr Pro Gly
1               5                   10

<210> SEQ ID NO 6
<211> LENGTH: 10
<212> TYPE: PRT
<213> ORGANISM: Lamprey

<400> SEQUENCE: 6

Glu His Trp Ser His Asp Trp Lys Pro Gly
1               5                   10

<210> SEQ ID NO 7
<211> LENGTH: 116
<212> TYPE: PRT
<213> ORGANISM: Homo sapiens

<400> SEQUENCE: 7

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
                20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
        50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
            100                 105                 110

Tyr His Lys Ser
        115

<210> SEQ ID NO 8
<211> LENGTH: 121
<212> TYPE: PRT
<213> ORGANISM: Homo sapiens

<400> SEQUENCE: 8

Ser Arg Glu Pro Leu Arg Pro Trp Cys His Pro Ile Asn Ala Ile Leu
1               5                   10                  15

Ala Val Glu Lys Glu Gly Cys Pro Val Cys Ile Thr Val Asn Thr Thr
                20                  25                  30

Ile Cys Ala Gly Tyr Cys Pro Thr Met Met Arg Val Leu Gln Ala Val
            35                  40                  45

Leu Pro Pro Leu Pro Gln Val Val Cys Thr Tyr Arg Asp Val Arg Phe
        50                  55                  60

Glu Ser Ile Arg Leu Pro Gly Cys Pro Arg Gly Val Asp Pro Val Val
65                  70                  75                  80

Ser Phe Pro Val Ala Leu Ser Cys Arg Cys Gly Pro Cys Arg Arg Ser

```
                            85                  90                  95
Thr Ser Asp Cys Gly Gly Pro Lys Asp His Pro Leu Thr Cys Asp His
            100                 105                 110

Pro Gln Leu Ser Gly Leu Leu Phe Leu
        115                 120

<210> SEQ ID NO 9
<211> LENGTH: 145
<212> TYPE: PRT
<213> ORGANISM: Homo sapiens

<400> SEQUENCE: 9

Ser Lys Glu Pro Leu Arg Pro Arg Cys Arg Pro Ile Asn Ala Thr Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Thr Arg Val Leu Gln Gly Val
        35                  40                  45

Leu Pro Ala Leu Pro Gln Val Val Cys Asn Tyr Arg Asp Val Arg Phe
    50                  55                  60

Glu Ser Ile Arg Leu Pro Gly Cys Pro Arg Gly Val Asn Pro Val Val
65                  70                  75                  80

Ser Tyr Ala Val Ala Leu Ser Cys Gln Cys Ala Leu Cys Arg Arg Ser
                85                  90                  95

Thr Thr Asp Cys Gly Gly Pro Lys Asp His Pro Leu Thr Cys Asp Asp
            100                 105                 110

Pro Arg Phe Gln Asp Ser Ser Ser Ser Lys Ala Pro Pro Pro Ser Leu
        115                 120                 125

Pro Ser Pro Ser Arg Leu Pro Gly Pro Ser Asp Thr Pro Ile Leu Pro
    130                 135                 140

Gln
145
```

METHODS FOR DIAGNOSING LHRH OR HCG/LH RECEPTOR EXPRESSING TUMORS, CANCERS AND NEOPLASIAS

RELATED APPLICATIONS

This patent application is a continuation of U.S. patent application Ser. No. 12/975,058, filed Dec. 21, 2010, which claims priority to U.S. Provisional Patent Application No. 61/289,010, filed Dec. 22, 2009. The entire contents of the foregoing applications are incorporated herein by reference, including all text, tables, sequence listings and drawings.

TECHNICAL FIELD

The invention relates to diagnosis, detection, screening, identifying and predicting methods. In various embodiments, methods of the invention include diagnosis, detection, screening for or imaging a hyperproliferative disorder (e.g., a tumor, cancer or neoplasia) in the subject; identifying a subject that will or is likely to respond to therapy for a hyperproliferative disorder (e.g., a tumor, cancer or neoplasia, or a metastasis thereof); and predicting therapeutic efficacy of a treatment for a hyperproliferative disorder (e.g., a tumor, cancer or neoplasia, or a metastasis thereof) in a subject.

INTRODUCTION

The need to develop new diagnosis, detection, screening, imaging, identification and predictive methods for hyperproliferative disorders (e.g., a tumor, cancer or neoplasia, or a metastasis thereof) is evident. For example, the five year survival rate is only 10-40% for patients with lung, colorectal, breast and prostate cancer if diagnosed with distant metastatic disease.

SUMMARY

The invention provides methods and kits for diagnosis, detection, screening and imaging, in vitro, ex vivo and in vivo. Methods include, among other things, contacting a sample (e.g., a biological sample) from or of a subject with an agent that detects the presence of one or more hormone receptors (e.g., LHRH- or hCG/LH receptors) in the sample, and correlating the amount or expression of hormone receptors (e.g., LHRH- or hCG/LH receptors) with the presence of or increased risk of having a hyperproliferative disorder (e.g., a tumor, cancer or neoplasia, or a metastasis thereof), thereby identifying the subject as having or at risk of having a hyperproliferative disorder (e.g., a tumor, cancer or neoplasia, or a metastasis thereof). Methods also include, among other things, administering an agent (e.g., a detectable or labeled agent) to a subject having or at risk of having a hyperproliferative disorder (e.g., a tumor, cancer or neoplasia, or a metastasis thereof) in an amount effective to diagnose, detect, screen for or image a hyperproliferative disorder (e.g., a tumor, cancer or neoplasia, or a metastasis thereof) in the subject. In particular aspects, a sample or a subject in which at least 1-25% of the cells express a hormone receptor (e.g., LHRH- or hCG/LH receptors) correlates with the presence or an increased risk of a hyperproliferative disorder (e.g., a tumor, cancer or neoplasia, or a metastasis thereof), or cells in the sample or subject express more of a hormone receptor (e.g., LHRH- or hCG/LH receptors), for example, the cells in the sample express at least 10%, 25%, 30%, 40%, 45%, or 50% or more of the hormone receptor than comparative control cells (e.g., normal cells), which correlates with the presence or an increased risk of a hyperproliferative disorder (e.g., a tumor, cancer or neoplasia, or a metastasis thereof) in the subject.

The invention also provides methods and kits for identifying a subject that will or is likely to respond to a treatment or a therapy that targets a receptor (e.g., a hormone receptor) or that targets a hyperproliferative disorder (e.g., a tumor, cancer or neoplasia, or a metastasis thereof), in vitro, ex vivo and in vivo. In one embodiment, a method includes, contacting a biological sample from a subject with an agent that detects the presence of a hormone receptor—the presence the hormone receptor (e.g., LHRH- or hCG/LH receptors) in the sample indicates that the subject will or is likely to respond to a treatment or therapy (e.g., for a hyperproliferative disorder such as a tumor, cancer or neoplasia, or a metastasis thereof) that targets the hormone receptor. In another embodiment, a method includes, administering an agent that detects the presence of a hormone receptor to a subject—the presence of the hormone receptor (e.g., LHRH- or hCG/LH receptors) in the subject indicates that the subject will or is likely to respond to a treatment or therapy (e.g., for a hyperproliferative disorder such as a tumor, cancer or neoplasia, or a metastasis thereof) that targets the hormone receptor.

The invention further provides in vitro, ex vivo and in vivo methods and kits for predicting therapeutic efficacy for a treatment or therapy that targets a receptor (e.g., a hormone receptor) or that targets a hyperproliferative disorder (e.g., a tumor, cancer or neoplasia, or a metastasis thereof). Methods include, among other things, contacting a biological sample from a subject with an agent that detects the presence of a hormone receptor, and correlating the amount of hormone receptor (e.g., LHRH- or hCG/LH receptors) present with the likelihood of therapeutic efficacy of treatment or therapy that targets the hormone receptor (e.g., LHRH- or hCG/LH receptors), thereby predicting the therapeutic efficacy of the treatment or therapy that targets the hormone receptor. In particular aspects, hormone receptor amounts in the sample greater than normal, such as hormone expressing cells in the sample or subject expressing more of a hormone receptor than is typically present in an appropriate control sample (e.g., normal cells), is predictive of therapeutic efficacy, for example, when 1% or more of the cells in the sample (e.g., 5%, 10%, 15%, 20%, 25%, 30%, etc. or more) express a hormone receptor, which is predictive of therapeutic efficacy for treatment that targets a hormone receptor or that targets a hyperproliferative disorder (e.g., a tumor, cancer or neoplasia, or a metastasis thereof).

Biological samples analyzed in accordance with the methods of the invention, and subjects treatable in accordance with the methods of the invention include, for example, an animal such as a mammalcells, or a cell, tissue or organ biopsy. In particular embodiments, a biological sample analyzed or a subject administered an agent is of an animal, such as a mammal (e.g., a human). Non-limiting biological sample can be from a reproductive cell, tissue or organ, such as breast, endometrium, uterus, ovary, testes, and other cells, tissues and organs, such as prostate, colon, pancreas, esophagus, liver, skin, kidney, adrenal gland, brain and blood.

Therapeutic efficacy for a treatment or therapy that targets a receptor (e.g., a hormone receptor) include, for example, a polypeptide that binds to the receptor, such as an antibody or receptor ligand, or a polynucleotide that hybridizes to a nucleic acid encoding all or a portion of a receptor. In particular embodiments, an agent includes a polypeptide that binds to an LHRH- or hCG/LH receptor, or a polynucleotide that hybridizes to a nucleic acid sequence encoding all or a portion of an LHRH- or hCG/LH receptor. Non-limiting examples of ligands include, for LHRH receptor for example, gonadotropin-releasing hormone I, gonadotropin-releasing hormone II, lamprey III luteinizing hormone releasing hormone, and fragments thereof; and for hCG/LH receptor, ligands include luteinizing hormone beta chain, luteinizing hormone (LH), chorionic gonadotropin (CG), chorionic gonadotropin beta subunit (β- orbeta-CG), and fragments thereof. Non-limiting examples of agents that bind to a receptor include, for LHRH receptor for example, leuprolide, leuprolide acetate (Lupron™), Goserelin (Zoladex™), Histrelin (Supprelin™), Triptorelin (Trelstar™), Buserelin (Suprefact™), Cetrorelix (Cetrotide™), Ganirelix (Antagon™), Antide, Abarelix (Plenaxis™), Teverelix (Antarelix™), Fe 200486 (Degarelix), Nal-Glu or Elagolix (NBI-56418) or an analog thereof.

Detection, diagnostic and imaging methods include, but are not limited to immunohistochemistry (IHC), in-situ hybridization (ISH), ELISA, immunoprecipitation, immunofluorescence, chemiluminescence, radioactivity, X-ray, nucleic acid hybridization, and protein-protein interaction. Detection, diagnostic and imaging methods also include, but are not limited to immunoprecipitation, ELISA, flow cytometry, Western blotting, polymerase chain reaction, DNA transcription, Northern blotting and Southern blotting.

Tumors, cancers and neoplasias can be present or affect and therefore be detected, diagnosed or imaged in breast, endometrium, uterus, ovary, testes, lung, prostate, colon, pancreas, esophagus, liver, skin, kidney, adrenal gland, brain, and which therefore include detection, diagnosis and imaging of lymphoma, breast, endometrium, uterus, ovary, testes, lung, prostate, colon, pancreas, esophagus, liver, skin, kidney, adrenal gland, and brain tumors, cancers and neoplasias. Tumors, cancers and neoplasias can be a metastasis or recurring tumor, cancer or neoplasia.

DETAILED DESCRIPTION

Figure 1:
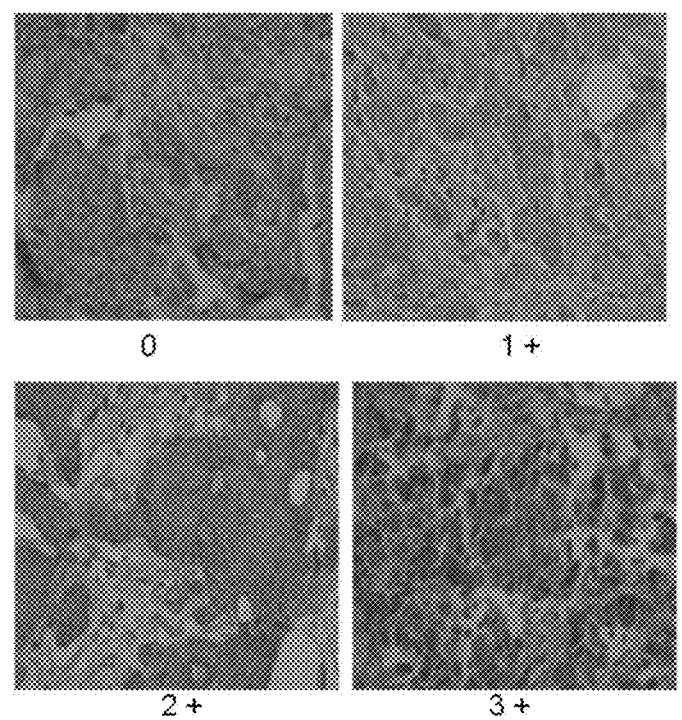
FIG. 1: Shows LHRH receptors in biopsies from breast cancer patients stained with anti-LHRH receptor monoclonal antibody, clone A9E4. Each panel shows the intensity of expression evaluated through the Ventana Image Analysis System (VIAS) adjunctive computer assisted image analysis system functionally connected to an interactive microscope (Axio Imager).

In accordance with the invention, there are provided methods and kits for diagnosis, detection, screening and imaging of a hyperproliferative disorder (e.g., a tumor, cancer or neoplasia, or metastasis thereof) in vitro, ex vivo and in vivo. In one embodiment, a method of the invention includes administering an agent to the subject under conditions whereby the agent can bind to a hyperproliferative cell (e.g., a tumor, cancer or neoplasia, or metastasis thereof), and detecting the agent in the subject to diagnose, detect, screen or image a hyperproliferative disorder (e.g., a tumor, cancer or neoplasia, or metastasis thereof) in the subject. In another embodiment, a method of the invention includes administering an agent to the subject under conditions whereby the agent can bind to a hyperproliferative cell (e.g., a tumor, cancer or neoplasia, or metastasis thereof), and detecting the agent in the subject to ascertain the presence or absence of hyperproliferative cells (e.g., a tumor, cancer or neoplasia, or metastasis thereof), thereby detecting hyperproliferative cells (e.g., a tumor, cancer or neoplasia, or metastasis thereof), or diagnosing the subject as having or not having hyperproliferative cells (e.g., a tumor, cancer or neoplasia, or metastasis thereof). In an additional embodiment, a method of the invention includes administering an agent to the subject under conditions whereby the agent can bind to hyperproliferative cells (e.g., a tumor, cancer or neoplasia, or metastasis thereof), and imaging the agent in the subject to ascertain the presence or absence, or the extent (progression or regression) or location of the hyperproliferative cells (e.g., a tumor, cancer or neoplasia, or metastasis thereof) in the subject.

Invention methods include, among other things, in vitro, ex vivo and in vivo contact and/or administration. A sample, such a biological sample, can be contacted with, administered, or delivered an agent in order to effect a method of the invention, for example, to diagnose, detect, screen for or to image a hyperproliferative disorder (e.g., a tumor, cancer or neoplasia, or metastasis thereof), to predict therapeutic efficacy of a treatment for a hyperproliferative disorder (e.g., a tumor, cancer or neoplasia, or metastasis thereof), or to predict therapeutic efficacy of a treatment that targets a receptor (e.g., hormone receptor). Subjects can also be contacted with, administered, or delivered an agent in order to effect a method of the invention, for example, to diagnose, detect, screen for or image a hyperproliferative disorder (e.g., a tumor, cancer or neoplasia, or metastasis thereof), to predict therapeutic efficacy of a treatment that targets a receptor (e.g., hormone receptor), or to predict therapeutic efficacy of a treatment for a hyperproliferative disorder (e.g., a tumor, cancer or neoplasia, or metastasis thereof).

The term "contact" and grammatical variations thereof means a sample or a subject is given or delivered an agent under conditions allowing a physical interaction (direct or indirect) between an agent and a receptor, such as a receptor expressed on a hyperproliferative cell (e.g., a tumor, cancer or neoplasia, or metastasis thereof), or a hyperproliferative cell, which may be present in the sample or in a subject. Contact as used herein includes in solution, in solid phase, in vitro, ex vivo, in a cell and in vivo. Thus, methods of the invention include contact of an agent with a target, such as a receptor (e.g., a hormone receptor) or cell (e.g., a hyperproliferative cell), under conditions allowing the agent to bind to the receptor or cell, if the receptor or cell are present in a sample or in a subject. The term "administering" includes delivery to a subject in which the agent can contact (e.g., physically interact, directly or indirectly) with a receptor (e.g., a hormone receptor) such as a receptor expressed on a hyperproliferative cell (e.g., a tumor, cancer or neoplasia, or metastasis thereof), or a hyperproliferative cell, in vivo, i.e., in the subject.

In particular embodiments of the invention, an agent is a molecule that binds, under appropriate conditions, to a receptor, such as a hormone receptor (e.g., expressed on a hyperproliferative cell), or to a hyperproliferative cell (e.g., a tumor, cancer or neoplasia, or metastasis thereof) and that is detectable. The term "bind," or "binding," when used in reference to an agent, means that the agent physically interacts (directly or indirectly) at the molecular level with a receptor protein or a receptor encoding nucleic acid sequence. Thus, an agent can bind to all or a part of receptor protein or nucleic acid sequence. Typically, binding is that which is specific or selective for the receptor or nucleic acid. Specific and selective binding can be distinguished from non-specific binding using assays known in the art (e.g., for protein detection, immunoprecipitation, ELISA, flow cytometry, and Western blotting, and for nucleic acid detection, polymerase chain reaction, DNA transcription, northern and southern blotting, etc.).

Agents include organic and inorganic molecules. Organic agents include, for example, polypeptide and nucleic acid sequences, and small organic ligands. Inorganic agents include, for example, metals, metal oxides, radioactive isotopes, fluorophores, chromophores, and electron-dense reagents.

As used herein, the terms "polypeptide" "protein," "peptide" and "amino acid sequence" are used interchangeably herein to refer to two or more amino acids, or "residues," covalently linked by an amide bond or equivalent. Residues of amino acid sequences can be linked by natural amide bonds, or by non-natural or non-amide chemical bonds.

Polypeptide agents include ligands, for example, a ligand or antibody that binds to a receptor (e.g., a hormone receptor such as LHRH- or hCG/LH receptors). Ligands also include hormones, which bind to hormone receptors include, for example, mammalian forms, such as primate (e.g., human) hormones.

Non-limiting exemplary receptor ligands for LHRH receptors, include gonadotropin-releasing hormone I, gonadotropin-releasing hormone II, lamprey III luteinizing hormone releasing hormone, and fragments thereof that bind to LHRH receptors. Non-limiting exemplary receptor ligands for hCG/LH include luteinizing hormone beta chain, luteinizing hormone (LH), chorionic gonadotropin (CG), chorionic gonadotropin beta subunit (β- or beta-CG), or fragments thereof that bind to hCG/LH receptors (e.g., chorionic gonadotropin beta subunit fragment 81-95).

Representative hormone receptors include, for example, LHRH (luteinizing hormone releasing hormone, aka gonadotropin-releasing hormone) receptor, and CG (chorionic gonadotropin hormone, aka luteinizing hormone) receptor. Hormone receptors include, for example, mammalian forms, such as primate (e.g., human) hormone receptors.

A representative human LHRH receptor sequence includes, but is not limited to, full length or a subsequence of (SEQ ID NO.:2):

```
  1  MANSASPEQN  QNHCSAINNS  IPLMQGNLPT  TLSGKIRVT  VTFFLFLLSA  TFNASFLLKL
 61  QKWTQKKEKG  KKLSRMKLLL  KHLTLANLLE  TLIVMPLDGM  WNITVQWYAG  ELLCKVLSYL
121  KLFSMYAPAF  MMVVISLDRS  LAITRPLALK  SNSKVGQSMV  GLAWILSSVF  AGPQLYIFRM
181  IHLADSSGQT  KVFSQCVTHC  SFSQWWHQAF  YNFFTFSCLF  IIPLFIMLIC  NAKIIFTLTR
241  VLHQDPHELQ  LNQSKNNIPR  ARLKTLKMTV  AFATSFTVCW  TPYYVLGIWY  WFDPEMLNRL
301  SDPVNHFFFL  FAFLNPCFDP  LIYGYFSL.
```

A representative hCG/LH human receptor sequence includes, but is not limited to, full length or a subsequence of (SEQ ID NO.: 3):

```
  1  MKQRFSALQL  LKLLLLLQPP  LPRALREALC  PEPCNCVPDG  ALRCPGPTAG  LTRLSLAYLP
 61  VKVIPSQAFR  GLNEVIKIEI  SQIDSLERIE  ANAFDNLLNL  SEILIQNTKN  LRYIEPGAFI
121  NLPRLKYLSI  CNTGIRKFPD  VTKVFSSESN  FILEICDNLH  ITTIPGNAFQ  GMNNESVTLK
181  LYGNGFEEVQ  SHAFNGTTLT  SLELKENVHL  EKMHNGAFRG  ATGPKTLDIS  STKLQALPSY
241  GLESIQRLIA  TSSYSLKKLP  SRETFVNLLE  ATLTYPSHCC  AFRNLPTKEQ  NFSHSISENF
301  SKQCESTVRK  VSNKTLYSSM  LAESELSGWD  YEYGFCLPKT  PRCAPEPDAF  NPCEDIMGYD
361  FLRVLIWLIN  ILAIMGNMTV  LFVLLTSRYK  LTVPRFLMCN  LSFADFCMGL  YLLLIASVDS
421  QTKGQYYNHA  IDWQTGSGCS  TAGFFTVFAS  ELSVYTLTVI  TLERWHTITY  AIHLDQKLRL
481  RHAILIMLGG  WLFSSLIAML  PLVGVSNYMK  VSICFPMDVE  TTLSQVYILT  ILILNVVAFF
541  IICACYIKIY  FAVRNPELMA  TNKDTKIAKK  MAILIFTDFT  CMAPISFFAI  SAAFKVPLIT
601  VTNSKVLLVL  FYPINSCANP  FLYAIFTKTF  QRDFFLLLSK  FGCCKRRAEL  YRRKDFSAYT
661  SNCKNGFTGS  NKPSQSTLKL  STLHCQGTAL  LDKTRYTEC.
```

Agents therefore include molecules that bind to hormone receptors, which include hormones and hormone subsequences. Non-limiting representative hormones include, for example, gonadotropin-releasing hormone I, gonadotropin-releasing hormone II, and lamprey III luteinizing hormone releasing hormone. Representative hormones also include, for example, luteinizing hormone (LH), luteinizing hormone beta chain, chorionic gonadotropin (CG), chorionic gonadotropin beta chain, follicle stimulating hormone (FSH), follicle stimulating hormone (FSH) beta chain, thyroid stimulating hormone (TSH), and thyroid stimulating hormone (TSH) beta chain. A representative subsequence is chorionic gonadotropin beta subunit, fragment 81-95.

The human luteinizing hormone (LH), chorionic gonadotropin (CG), follicle stimulating hormone (FSH), and thyroid stimulating hormone (TSH) are dimers consisting of alpha and beta subunits which associate noncovalently. The alpha subunits of these hormones are all the same, but their beta chains are different and confer specificity.

A representative human gonadotropin-releasing hormone I sequence includes, but is not limited to, full length or a subsequence of (SEQU ID NO.:4): 1 pGlu (E)HWSYGLRPG A representative human gonadotropin-releasing hormone II sequence includes, but is not limited to, full length or a subsequence of (SEQ ID NO.: 5): 1 pEHWSHGWYPG A representative lamprey III luteinizing hormone releasing hormone sequence includes, but is not limited to, full length or a subsequence of (SEQ ID NO.: 6): pEHWSHDWKPG.

A representative luteinizing hormone (LH), chorionic gonadotrophin (CG), follicle stimulating hormone (FSH), and thyroid stimulating hormone (TSH) alpha subunit (precursor) sequence includes, but is not limited to, full length or a subsequence of (SEQ ID NO.: 7):

```
MDYYRKYAAI FLVTLSVFLH VLHSAPDVQD CPECTLQENP
FFSQPGAPIL QCMGCCFSRA YPTPLRSKKT MLVQKNVTSE
STCCVAKSYN RVTVMGGFKV ENHTACHCST CYYHKS
```

A representative luteinizing hormone (LH) beta sequence includes, but is not limited to, full length or a subsequence of (SEQ ID NO.: 8):

```
SREPLRPWCH PINAILAVEK EGCPVCITVN TTICAGYCPT
MMRVLQAVLP PLPQVVCTYR DVRFESIRLP GCPRGVDPVV
SFPVALSCRC GPCRRSTSDC GGPKDHPLTC DHPQLSGLLF L.
```

A representative chorionic gonadotrophin (CG) beta sequence includes, but is not limited to, full length or a subsequence (e.g., fragment 81-95, SYAVALSCQCA-LARR) of (SEQ ID NO.: 9):

```
  1  SKEPLRPRCR PINATLAVEK EGCPVCITVN TTICAGYCPT

61  MTRVLQGVLP ALPQVVCNYR DVRFESIRLP GCPRGVNPVV SYAVALSCQC ALCRRSTTDC

121  GGPKDHPLTC DDPRFQDSSS SKAPPPSLPS PSRLPGPSDT PILPQ.
```

Polypeptide agents further include antibodies. As used herein the term "antibody" refers to a protein that binds to other molecules (antigens) via heavy and light chain variable domains, $V_H$ and $V_L$, respectively. Antibodies include full-length antibodies that include two heavy and two light chain sequences. Antibodies can have kappa or lambda light chain sequences, either full length as in naturally occurring antibodies, mixtures thereof (i.e., fusions of kappa and lambda chain sequences), and subsequences/fragments thereof.

Antibodies include monoclonal and polyclonal immunoglobulin molecules that belong to any class such as IgM, IgG, IgA, IgE, IgD, and any subclass thereof. Exemplary subclasses for IgG are $IgG_1$, $IgG_2$, $IgG_3$ and $IgG_4$.

A "monoclonal" antibody refers to an antibody that is based upon, obtained from or derived from a single clone, including any eukaryotic, prokaryotic, or phage clone. A "monoclonal" antibody is therefore defined structurally, and not the method by which it is produced.

Antibodies also include subsequences and fragments that bind to the receptor or hyperproliferative cell. Antibody subsequences and fragments, including single-chain antibodies, can include all or a portion of heavy or light chain variable region sequences (e.g., CDR1, CDR2 or CDR3 in a heavy chain variable region sequence or in a light chain variable region sequence) alone or in combination with all or a portion of one or more of the following: hinge region, CH1, CH2, and CH3 domains. Non-limiting representative subsequences and fragments of an antibody include but are not limited to Fab, Fab', F(ab')$_2$, Fv, Fd, single-chain Fv (scFv), disulfide-linked Fvs (sdFv), $V_L$, $V_H$, trispecific (Fab$_3$), bispecific (Fab$_2$), diabody (($V_L$-$V_H$)$_2$ or ($V_H$-$V_L$)$_2$), triabody (trivalent), tetrabody (tetravalent), minibody ((scFv-$C_H$3)$_2$), bispecific single-chain Fv (Bis-scFv), IgGdeltaCH2, scFv-Fc, (scFv)$_2$-Fc and IgG4PE.

Antibodies include mammalian, primatized, humanized, fully human antibodies and chimeras. A mammalian antibody is an antibody which is produced by a mammal, transgenic or non-transgenic, or a non-mammalian organism engineered to produce a mammalian antibody, such as a non-mammalian cell (bacteria, yeast, insect cell), animal or plant.

A "human" antibody means that the amino acid sequence of the antibody is fully human, i.e., human heavy and human light chain variable and human constant regions. Thus, all of the amino acids are human or exist in a human antibody. An antibody that is non-human may be made fully human by substituting the non-human amino acid residues with amino acid residues that exist in a human antibody. Amino acid residues present in human antibodies, CDR region maps and human antibody consensus residues are known in the art (see, e.g., Kabat, *Sequences of Proteins of Immunological Interest,* 4th Ed.US Department of Health and Human Services. Public Health Service (1987); Chothia and Lesk (1987). A consensus sequence of human $V_H$ subgroup III, based on a survey of 22 known human $V_H$ III sequences, and a consensus sequence of human $V_L$ kappa-chain subgroup I, based on a survey of 30 known human kappa I sequences is described in Padlan *Mol. Immunol.* 31:169 (1994); and Padlan *Mol. Immunol.* 28:489 (1991). Human antibodies therefore include antibodies in which one or more amino acid residues have been substituted with one or more amino acids present in any other human antibody.

A "humanized" antibody, means that the amino acid sequence of the antibody has non-human amino acid residues (e.g., mouse, rat, goat, rabbit, etc.) of one or more complementarity determining regions (CDRs) that specifically bind to the desired antigen in an acceptor human immunoglobulin molecule, and one or more human amino acid residues in the Fv framework region (FR), which are amino acid residues that flank the CDRs. Such antibodies typically have reduced immunogenicity and therefore a longer half-life in humans as compared to the non-human parent antibody from which one or more CDRs were obtained or are based upon.

Antibodies include those referred to as "primatized," which are "humanized" except that the acceptor human immunoglobulin molecule and framework region amino acid residues may be any primate amino acid residue (e.g., ape, gibbon, gorilla, chimpanzees orangutan, macaque), in addition to any human residue. Human FR residues of the immunoglobulin can be replaced with corresponding non-human residues. Residues in the CDR or human framework regions can therefore be substituted with a corresponding residue from the non-human CDR or framework region donor antibody to alter, generally to improve, antigen affinity or specificity, for example. A humanized antibody may include residues, which are found neither in the human antibody nor in the donor CDR or framework sequences. For example, a FR substitution at a particular position that is not found in a human antibody or the donor non-human antibody may be predicted to improve binding affinity or specificity human antibody at that position. Antibody framework and CDR substitutions based upon molecular modeling are well known in the art, e.g., by modeling of the interactions of the CDR and framework residues to identify framework residues important for antigen binding and sequence comparison to identify unusual framework residues at particular positions (see, e.g., U.S. Pat. No. 5,585,089; and Riechmann et al., Nature 332:323 (1988)).

A "chimeric" antibody, means that the amino acid sequence of the antibody contains one or more portions that are derived from, obtained or isolated from, or based upon two or more different species. For example, a portion of the antibody may be human (e.g., a constant region) and another portion of the antibody may be non-human (e.g., a murine heavy or murine light chain variable region). Thus, an example of a chimeric antibody is an antibody in which different portions of the antibody are of different species origins. Unlike a humanized or primatized antibody, a chimeric antibody can have the different species sequences.

Organic agents further include small organic ligands. Non-limiting exemplary small organic ligand agents include, for LHRH receptors, leuprolide, leuprolide acetate (Lupron™), Goserelin (Zoladex™), Histrelin (Supprelin™) Triptorelin (Trelstar™), Buserelin (Suprefact™), Cetrorelix (Cetrotide™), Ganirelix (Antagon™), Antide, Abarelix (Plenaxis™), Teverelix (Antarelix™), Fe 200486 (Degarelix), Nal-Glu and Elagolix (NBI-56418).

Organic agents also include nucleic acid sequences. As used herein, the terms "nucleic acid" and "polynucleotide" and the like refer to at least two or more ribo- or deoxyribonucleic acid base pairs (nucleotides) that are linked through a phosphoester bond or equivalent covalent bond. Nucleic acids include polynucleotides and polynucleosides. Nucleic acids include single, double or triplex, circular or linear, molecules. Exemplary nucleic acids include but are not limited to: RNA, DNA, cDNA, genomic nucleic acid, naturally occurring and non naturally occurring nucleic acid, e.g., synthetic nucleic acid.

Nucleic acid agents include, for example, polynucleotides that hybridizes to a nucleic acid sequence encoding all or a portion of a receptor (e.g., a hormone receptor such as LHRH- or hCG/LH receptors). As representative protein sequences for various hormone receptors and homones are disclosed herein or known to the skilled artisan, nucleic acids that hybridize to such sequences can be used in the methods of the invention for detecting receptors, including hormone receptors.

In order to detect a receptor, a nucleic acid can term "hybridize" to all or a protion of the receptor encoding nucleic acid, which refers to the binding between two or more nucleic acid sequences. Hybridizing sequences will generally be more than about 50% complementary to all or a portion of a nucleic acid that encodes the receptor. The hybridization region between hybridizing sequences typically is at least about 10-15 nucleotides, 15-20 nucleotides, 20-30 nucleotides, 30-50 nucleotides, 50-100 nucleotides, 100 to 200 nucleotides or more, or any numerical value or range within or encompassing such lengths.

The term "complementary" or "antisense" refers to a polynucleotide or peptide nucleic acid (PNA) capable of binding to a specific DNA or RNA sequence. Antisense includes single, double, triple or greater stranded RNA and DNA polynucleotides and peptide nucleic acids (PNAs) that bind RNA transcript or DNA. Particular examples include RNA and DNA antisense that binds to sense RNA. For example, a single stranded nucleic acid can target a transcript that encodes a receptor. Antisense molecules are typically 90-100% complementary to the sense strand but can be "partially" complementary, in which only some of the nucleotides bind to the sense molecule (less than 100% complementary, e.g., 95%, 90%, 80%, 70% and sometimes less), or any numerical value or range within or encompassing such percent values.

Nucleic acids can be of various lengths. Nucleic acid lengths typically range from about 10 nucleotides to 20 Kb, or any numerical value or range within or encompassing such lengths, e.g.,10 nucleotides to 10 Kb, 1 to 5 Kb or less, 1000 to about 500 nucleotides or less in length. Nucleic acids can also be shorter, for example, 100 to about 500 nucleotides, or from about 10 to 25, 25 to 50, 50 to 100, 100 to 250, or about 250 to 500 nucleotides in length, or any numerical value or range or value within or encompassing such lengths. In particular aspects, a nucleic acid sequence has a length from about 10-20, 20-30, 30-50, 50-100, 100-150, 150-200, 200-250, 250-300, 300-400, 400-500, 500-1000, 1000-2000, nucleotides, or any numerical value or range within or encompassing such lengths. Shorter polynucleotides are commonly referred to as "oligonucleotides" or "probes" of single- or double-stranded DNA. However, there is no upper limit to the length of such oligonucleotides.

Nucleic acid sequences can include nucleotide and nucleoside substitutions, additions and deletions, as well as derivatized forms and fusion/chimeric sequences (e.g., encoding recombinant polypeptide). For example, due to the degeneracy of the genetic code, nucleic acids include sequences and subsequences degenerate with respect to nucleic acids that encode a receptor and subsequences thereof, such as the hormone receptors set forth herein, as well as variants and modifications thereof (e.g., substitutions, additions insertions and deletions).

Nucleic acids can be produced using various standard cloning and chemical synthesis techniques. Techniques include, but are not limited to nucleic acid amplification, e.g., polymerase chain reaction (PCR), with genomic DNA or cDNA targets using primers (e.g., a degenerate primer mixture) capable of annealing to antibody encoding sequence. Nucleic acids can also be produced by chemical synthesis (e.g., solid phase phosphoramidite synthesis) or transcription from a gene. The sequences produced can then be translated in vitro, or cloned into a plasmid and propagated and then expressed in a cell (e.g., a host cell such as eukaryote or mammalian cell, yeast or bacteria, in an animal or in a plant).

Agents include modifications or variations, such as substitutions, additions and deletions as long as such modifications, variations, substitutions, additions and deletions do not destroy activity, e.g., binding activity. Such agents therefore include subsequences and amino acid and nucleic acid substitutions of the sequences set forth herein, such as a polypeptide agent (e.g., a hormone) that binds to a target (e.g., receptor), or a nucleic acid agent that binds to a target nucleic acid sequence that encodes a receptor (e.g., a hormone receptor). In particular embodiments, a subsequence of an agent has 5 to 10, 10 to 15, 15 to 20, 20 to 25, 25 to 30, 30 to 35 or more amino acid or nucleotide residues.

Specific examples include a substitution or deletion of one or more amino acid (e.g., 1-3, 3-5, 5-10, 10-20, or more) residues of a polypeptide. A "conservative amino acid substitution" is a replacement of one amino acid by a biologically, chemically or structurally similar residue. Biologically similar means that the substitution is compatible with a biological activity, e.g., binding activity. Structurally similar means that the amino acids have side chains with similar length, such as alanine, glycine and serine, or having similar size, or a structure is maintained. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, etc.

A modified agent, such as a hormone, can have a sequence with 50%, 60%, 70%, 75%, 80%, 85%, 90%, 95%, 96%, 97%, 98%, or more identity to a reference sequence (e.g., a hormone sequence). Due to variation in the amount of sequence conservation between structurally and functionally related proteins, the amount of sequence identity required to retain a function or activity (e.g., binding) depends upon the protein, the region and the function or activity of that region.

The term "identity" and "homology" and grammatical variations thereof mean that two or more referenced entities are the same. Thus, where two sequences are identical, they have the same amino acid sequence. "Areas, regions or domains of identity" mean that a portion of two or more referenced entities are the same. Thus, where two sequences are identical or homologous over one or more sequence regions, they share identity in these regions.

The extent of identity between two sequences can be ascertained using a computer program and mathematical algorithm known in the art. Such algorithms that calculate percent sequence identity (homology) generally account for sequence gaps and mismatches over the comparison region. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., *Proc. Natl. Acad. Sci. USA* 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

Modified polypeptide agents also include one or more D-amino acids substituted for L-amino acids (and mixtures thereof), structural and functional analogues, for example, peptidomimetics having synthetic or non-natural amino acids or amino acid analogues and derivatized forms. For example, a polypeptide can have 1 to 5, 5 to 10, 10 to 15, 15 to 20, 20 to 25, 25 to 30, 30 to 35, 35 to 50, 50 to 100 L or D amino acid residues, or a combination of L- and D-amino acids or more amino acid residues.

Modifications include cyclic structures such as an end-to-end amide bond between the amino and carboxy-terminus of the molecule or intra- or inter-molecular disulfide bond. Polypeptides may be modified in vitro or in vivo, e.g., post-translationally modified to include, for example, sugar residues, phosphate groups, ubiquitin, fatty acids, lipids, etc. Polypeptide non-amide chemical bonds include, for example, those formed with glutaraldehyde, N-hydroxysuccinimide esters, bifunctional maleimides, N, N'-dicyclohexylcarbodiimide (DCC), ketomethylene, aminomethylene, olefin, ether, thioether and the like (see, e.g., Spatola in *Chemistry and Biochemistry of Amino Acids, Peptides and Proteins*, Vol. 7, pp 267-357 (1983), "Peptide and Backbone Modifications," Marcel Decker, NY).

Polypeptides and peptidomimetics can be produced and isolated using methods known in the art. Peptides can be synthesized, whole or in part, using chemical methods known in the art (see, e.g., Caruthers (1980). *Nucleic Acids Res. Symp. Ser.* 215; Horn (1980); and Banga, A. K., *Therapeutic Peptides and Proteins, Formulation, Processing and Delivery Systems* (1995) Technomic Publishing Co., Lancaster, Pa.). Peptide synthesis can be performed using various solid-phase techniques (see, e.g., Roberge *Science* 269:202 (1995); Merrifield, *Methods Enzymol.* 289:3(1997)) and automated synthesis may be achieved, e.g., using the ABI 431A Peptide Synthesizer (Perkin Elmer) in accordance with the manufacturer's instructions. Peptides and peptidomimetics can also be synthesized using combinatorial methodologies. Synthetic residues and polypeptides incorporating mimetics can be synthesized using a variety of procedures and methodologies known in the art (see, e.g., *Organic Syntheses* Collective Volumes, Gilman, et al. (Eds) John Wiley & Sons, Inc., NY). Modified peptides can be produced by chemical modification methods (see, for example, Belousov, *Nucleic Acids Res.* 25:3440 (1997); Frenkel, *Free Radic. Biol. Med.* 19:373 (1995); and Blommers, *Biochemistry* 33:7886 (1994).

An agent as defined herein is detectable. An agent can be labeled in order to be detectable. A label or a tag can be used to provide an agent that is detectable. Detectable labels include labels suitable for diagnosis, detection, screening and imaging. A detectable label can be attached to (e.g., linked conjugated) an agent, or be within or be one or more atmoms that comprise the agent. As the structure of agents can include one or more of carbon, hydrogen, nitrogen, oxygen, sulfur, phosphorous, etc., radioisotopes of any of carbon, hydrogen, nitrogen, oxygen, sulfur, phosphorous, etc., can be included within an agent detectably labelled.

Non-limiting exemplary detectable labels also include a radioactive material, such as a radioisotope, a metal or a metal oxide. Radioisotopes include radionuclides emitting alpha, beta or gamma radiation. In diagnostic, screening, detection and imaging methods, typically a beta emitter is employed. In particular embodiments, a radioisotope can be one or more of: C, N, O, H, S, Cu, Fe, Ga, Ti, Sr, Y, Tc, In, Pm, Gd, Sm, Ho, Lu, Re, At, Bi or Ac. In additional embodiments, a radioisotope can be one or more of: $^{3}$H, $^{10}$B, $^{18}$F, $^{11}$C, $^{14}$C, $^{13}$N, $^{18}$O, $^{15}$O, $^{32}$P, $^{35}$S, $^{35}$Cl, $^{45}$Ti, $^{46}$Si, $^{51}$Cr, $^{52}$Fe, $^{59}$Fe, $^{57}$Co, $^{60}$Cu, $^{61}$Cu, $^{62}$Cu, $^{64}$Cu, $^{67}$Cu, $^{67}$Ga, $^{68}$Ga, $^{72}$As, $^{76}$Br, $^{77}$Br, $^{81m}$Kr, $^{82}$Rb, $^{85}$Sr, $^{89}$Sr, $^{86}$Y, $^{90}$Y, $^{95}$Nb, $^{94m}$Tc, $^{99m}$Tc, $^{97}$Ru, $^{103}$Ru, $^{105}$Rh, $^{109}$Cd, $^{111}$In, $^{113}$Sn, $^{113m}$In, $^{114}$In, $^{140}$La, $^{141}$Ce, $^{149}$Pm, $^{153}$Gd, $^{157}$Gd, $^{153}$Sm, $^{161}$Tb, $^{166}$Dy, $^{166}$Ho, $^{169}$Er, $^{169}$Y, $^{175}$Yb, $^{177}$Lu, $^{186}$Re, $^{188}$Re, $^{201}$Tl, $^{203}$Pb, $_{211}$At, $^{212}$Bi or $^{225}$Ac.

Additional non-limiting exemplary detectable labels include a metal or a metal oxide. In particular embodiments, a metal or metal oxide is one or more of: gold, silver, copper, boron, manganese, gadolinium, iron, chromium, barium, europium, erbium, praseodynium, indium, or technetium. In additional embodiments, a metal oxide includes one or more of: Gd(III), Mn(II), Mn(III), Cr(II), Cr(III), Cu(II), Fe (III), Pr(III), Nd(III) Sm(III), Tb(III), Yb(III) Dy(III), Ho(III), Eu(II), Eu(III), or Er(III). Metals and oxides include crystals.

Further non-limiting exemplary detectable labels include contrast agents (e.g., gadolinium; manganese; barium sulfate; an iodinated or noniodinated agent; an ionic agent or nonionic agent); magnetic and paramagnetic agents (e.g., iron-oxide chelate); nanoparticles; an enzyme (horseradish peroxidase, alkaline phosphatase, β-galactosidase, or acetylcholinesterase); a prosthetic group (e.g., streptavidin/biotin and avidin/biotin); a fluorescent material (e.g., umbelliferone, fluorescein, fluorescein isothiocyanate, rhodamine, dichlorotriazinylamine fluorescein, dansyl chloride or phycoerythrin); a luminescent material (e.g., luminol); or a bioluminescent material (e.g., luciferase, luciferin, aequorin). A label can be any imaging agent that can be employed for detection, screening, diagnostis, or imaging (e.g., for computed axial tomography (CAT or CT), fluoroscopy, single photon emission computed tomography (SPECT) imaging, optical imaging, positron emission tomography (PET), magnetic resonance imaging (MRI), gamma imaging).

A detectable label can also be linked or conjugated (e.g., covalently) to the agent. In various embodiments a detectable label, such as a radionuclide or metal or metal oxide can be bound or conjugated to the agent, either directly or indirectly. A linker or an intermediary functional group can be used to link an agent to a detectable label.

Linkers include amino acid or peptidomimetic sequences inserted between an agent and a label so that the two entities maintain, at least in part, a distinct function or activity. Linkers may have one or more properties that include a flexible conformation, an inability to form an ordered secondary structure or a hydrophobic or charged character which could promote or interact with either domain Amino acids typically found in flexible protein regions include Gly, Asn and Ser. Other near neutral amino acids, such as Thr and Ala, may also be used in the linker sequence. The length of the linker sequence may vary without significantly affecting a function or activity.

Linkers further include chemical moieties, conjugating agents, and intermediary functional groups. Such linkers are often used to bind radioisotopes which exist as, for example, metallic ions (e.g, cations) that bind to groups on the agent. Examples include moieties that react with free or semi-free amines, oxygen, sulfur, hydroxy or carboxy groups. Such functional groups therefore include mono and bifunctional crosslinkers, such as sulfo-succinimidyl derivatives (sulfo-SMCC, sulfo-SMPB), in particular, disuccinimidyl suberate (DSS), BS3 (Sulfo-DSS), disuccinimidyl glutarate (DSG) and disuccinimidyl tartrate (DST). Non-limiting examples include diethylenetriaminepentaacetic acid (DTPA) and ethylene diaminetetracetic acid (EDTA).

Biological samples include any sample capable of having a biological material. Specific non-limiting examples of biological samples include mucus, saliva, feces, blood, serum, plasma, cerebrospinal fluid, urine, or placenta. Biological samples also include biopsies, such as a cell, tissue or an organ biopsy, for example. Non-limiting samples including biopsies are of skin, dermis, breast, genito-urinary tract (uterus, ovary, endometrium, vagina, cervix, fallopian tube, bladder, testicle, penis, urinary tract, prostate), lung, nasopharynx, nose or sinuses, thyroid, head, neck, adrenal gland, thyroid, lymph, gastrointestinal tract (stomach, intestine, colon), kidney, pancreas, adrenal gland, liver, bone, bone marrow, heart, muscle, or a sample of the hematopoetic system.

A biological sample typically includes cells or cellular material. Cells that express a receptor, such as a hormone receptor, for example, a sex or gonadal steroid hormone receptor that can be targeted by an agent in accordance with methods of the invention also include reproductive cells, tissues and organs, such as breast, ovarian, uterine, cervical, endometrial, prostate, and testicular cells, tissues and organs, as well as non-reproductive cells, tissues and organs, such as pancreas, skin, liver, colon, kidney, esophagus, brain, blood cells, adrenal, pituitary gland, etc.

In methods of the invention, where a certain amount of expression of a receptor (e.g., a hormone receptor) is predictive or correlates with the presence of a hyperproliferative disorder (e.g., a tumor, cancer or neoplasia, or metastasis thereof), or that is predictive or correlates with therapeutic efficacy of a hyperproliferative disorder (e.g., a tumor, cancer or neoplasia, or metastasis thereof) treatment or therapy, the cells of the disorder typically express greater amounts of the receptor (e.g., hormone receptor) than normal cells. For example, cells of a hyperproliferative disorder (e.g., a tumor, cancer or neoplasia, or metastasis thereof) may express a hormone receptor that is not typically detectably expressed by normal comparison cells. Alternatively, or in addition, cells of a hyperproliferative disorder (e.g., a tumor, cancer or neoplasia, or metastasis thereof) may express greater amounts of a receptor (e.g., hormone receptor) than the amount of receptor that is typically expressed by normal comparison cells. In either case, expression of a receptor not normally expressed in normal cells, or where amounts of the receptor are greater than in normal cells, can reveal the presence of a hyperproliferative disorder (e.g., a tumor, cancer or neoplasia, or metastasis thereof) thereby identifying a subject that will or is likely to respond to a given treatment or therapy that targets a receptor (e.g., treatment of a hyperproliferative disorder), or correlate with and therefore be predictive of therapeutic efficacy of a hyperproliferative disorder (e.g., a tumor, cancer or neoplasia, or metastasis thereof) treatment or therapy.

In particular non-limiting aspects, to identify a subject that will or is likely to respond to a given treatment or therapy that targets a receptor (e.g., treatment of a hyperproliferative disorder), or for a prediction or correlation with therapeutic efficacy of treatment, at least 10%, 20%, 25%, 30%, 40%, 50%, 60%, 70%, 80%, 90% or more of the cells express a hormone receptor (e.g., LHRH- or hCG/LH receptors), than normal cells. In additional particular non-limiting aspects, for a prediction or correlation with therapeutic efficacy, expression of a hormone receptor (e.g., LHRH- or hCG/LH receptors) is at least 25%, 30%, 40%, 50%, 60%, 70%, 80%, 90% more than normal cells (i.e., the cells express at least 50% more of a hormone receptor, such as a LHRH- or hCG/LH receptor, than control cells).

Treatments whose therapeutic efficacy can be predicted based upon receptor expression include LHRH agonists (such as leuprolide, goserelin, buserelin, triptorelin, histrelin and the like) or LHRH antagonists (such as Abarelix, Cetrorelix, Ganirelix, Fe 200486 (Degarelix), Teverelix, Elagolix, Antide and the like) and hCG/LH receptor antisense nucleic acids, polypeptides that bind to LHRH- or hCG/LH receptors and fusion proteins (chimera) that contain LHRH or hCG/LH or their fragments.

Treatments whose therapeutic efficacy can also be predicted based upon receptor expression include a treatment with a chimera that targets LHRH- or hCG/LH receptors, for example, a chimera that includes a first sequence that binds to LHRH- or hCG/LH receptors, and a second cytotoxic moiety conjugated to said first sequence (e.g., a lytic peptide sequence, a radioisotope, ricin, diphtheria, gelonin, or granzyme B).

A "hyperproliferative cell" or "hyperproliferative disorder" refers to any undesirable or aberrant cell survival (e.g., failure to undergo cell differentiation, programmed cell death or apoptosis), growth or proliferation. Such disorders include benign hyperplasias, non-metastatic and metastatic neoplasias, cancers, tumors and malignancies. Undesirable or aberrant cell proliferation and hyperproliferative disorders can affect any cell, tissue, organ in a subject. Undesirable or aberrant cell proliferation and hyperproliferative disorders can be present in a subject, locally, regionally or systemically. A hyperproliferative disorder can arise from a multitude of tissues and organs, including but not limited to reproductive tissues and organs, breast, genito-urinary tract (uterus, ovary, vagina, cervix, endometrium, fallopian tube, bladder, testicle, penis, prostate), lung (e.g., small cell or non-small cell), thyroid, head and neck, brain, nasopharynx, throat, nose or sinuses, lymphoid, adrenal gland, pituitary gland, thyroid, lymph, gastrointestinal (mouth, esophagus, stomach, duodenum, ileum, jejunum (small intestine), colon, rectum), kidney, pancreas, liver, bone, bone marrow, lymph, blood, muscle, skin, and stem cells, which may or may not metastasize to other secondary sites, regions or locations.

The terms "tumor," "cancer" and "neoplasia" are used interchangeably and refer to a cell or population of cells whose growth, proliferation or survival is greater than growth, proliferation or survival of a normal counterpart cell, e.g. a cell proliferative, hyperproliferative or differentiative disorder. Typically, the growth is uncontrolled. The term "malignancy" refers to invasion of nearby tissue. The term "metastasis" or a secondary, recurring or recurrent tumor, cancer or neoplasia refers to spread or dissemination of a tumor, cancer or neoplasia to other sites, locations or regions within the subject, in which the sites, locations or regions are distinct from the primary tumor or cancer.

Invention methods include diagnosing, detecting, screening for, or imaging a primary neoplasia, tumor cancer and metastasis thereof. Metastasis include spreading to other sites, or the formation or establishment of neoplasia, tumors or cancers at other sites distal from the primary neoplasia, tumor or cancer. Thus, methods of the invention include, amoung other things, diagnosing, detecting, screening for, or imaging a metastases arising from a primary neoplasia, tumor or cancer to one or more other sites, locations or regions distinct from the primary neoplasia, tumor or cancer, growth or proliferation of a metastasis at one or more other sites, locations or regions distinct from the primary neoplasia, tumor or cancer, and formation or establishment of additional metastasis.

Neoplasias, tumors and cancers that can be diagnosed, detected, screened for, or imaged include sarcoma, carcinoma, adenocarcinoma, melanoma, myeloma, blastoma, glioma, lymphoma or leukemia. Exemplary cancers include, for example, carcinoma, sarcoma, adenocarcinoma, melanoma, neural (blastoma, glioma), mesothelioma and reticuloendothelial, lymphatic or haematopoietic neoplastic disorders (e.g., myeloma, lymphoma or leukemia).

Neoplasia, tumors and cancers include benign, malignant, metastatic and non-metastatic types, and include any stage (I, II, III, IV or V) or grade (G1, G2, G3, etc.) of neoplasia, tumor, or cancer, or a neoplasia, tumor, cancer or metastasis that is progressing, worsening, stabilized or in remission.

A "solid neoplasia, tumor or cancer" refers to neoplasia, tumor or cancer (e.g., metastasis) that typically aggregates together and forms a mass. Specific examples include visceral tumors such as melanomas, breast, pancreatic, uterine and ovarian cancers, testicular cancer, including seminomas, gastric or colon cancer, hepatomas, adrenal, renal and bladder carcinomas, lung, head and neck cancers and brain tumors/cancers.

Carcinomas refer to malignancies of epithelial or endocrine tissue, and include respiratory system carcinomas (lung, small cell lung), gastrointestinal system carcinomas, genito-urinary system carcinomas, testicular carcinomas, breast carcinomas, prostatic carcinomas, endocrine system carcinomas, and melanomas. The term also includes carcinosarcomas, e.g., which include malignant tumors composed of carcinomatous and sarcomatous tissues. Adenocarcinoma includes a carcinoma of a glandular tissue, or in which the tumor forms a gland like structure. Melanoma refers to malignant tumors of melanocytes and other cells derived from pigment cell origin that may arise in the skin, dermis, eye (including retina), or other regions of the body. Additional carcinomas can form from the uterine/cervix, endometrium, lung, head/neck, colon, pancreas, testes, adrenal gland, kidney, esophagus, stomach, liver and ovary.

Sarcomas refer to malignant tumors of mesenchymal cell origin. Exemplary sarcomas include for example, lymphosarcoma, liposarcoma, osteosarcoma, chondrosarcoma, leiomyosarcoma, rhabdomyosarcoma and fibrosarcoma.

Neural neoplasias include glioma, glioblastoma, meningioma, neuroblastoma, retinoblastoma, astrocytoma, oligodendrocytoma Specific non-limiting examples of neoplasias, tumors and cancers include malignant and non-malignant neoplasias, tumors and cancers, and metastasis. In particular, a neoplasia, tumor, cancer or metastasis of any stage (e.g., stages IA, IB, IIA, IIB, IIIA, IIIB or IV) or grade (e.g., grades G1, G2 or G3).

A "liquid neoplasia, tumor or cancer" refers to a neoplasia, tumor or cancer of the reticuloendothelial or hematopoetic system, such as a lymphoma, myeloma, or leukemia, or a neoplasia that is diffuse in nature. Particular examples of leukemias include acute and chronic lymphoblastic, myeolblastic and multiple myeloma. Typically, such diseases arise from poorly differentiated acute leukemias, e.g., erythroblastic leukemia and acute megakaryoblastic leukemia. Specific myeloid disorders include, but are not limited to, acute promyeloid leukemia (APML), acute myelogenous leukemia (AML) and chronic myelogenous leukemia (CML); lymphoid malignancies include, but are not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Specific malignant lymphomas include, non-Hodgkin lymphoma and variants, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

A tumor, cancer or neoplasia, or a metastasis thereof may arise from or may affect any part of the body of a subject. Exemplary parts (e.g., organ, tissue) affected include reproductive organs and tissues, skin, dermis, breast, lung, nasopharynx, nose or sinuses, thyroid, head, neck, brain, spine, adrenal gland, thyroid, lymph, blood, gastrointestinal (mouth, esophagus, stomach, duodenum, ileum, jejunum (small intestine), colon, rectum), genito-urinary tract (uterus, ovary, endometrium, vagina, cervix, fallopian tube, bladder, testicle, penis, urinary tract, prostate), kidney, pancreas, adrenal gland, liver, bone, bone marrow, heart, muscle, and the hematopoetic system. Thus, a method of the invention may be performed to diagnose, detect, screen, or image a tumor, cancer or neoplasia, or a metastasis thereof in the whole body of a subject, a particular region or general area, a specific organ or tissue, or a local portion of a region, organ or tissue.

Methods of the invention include detecting the type, kind, presence or absence, progression, regression or response, location or extent of a tumor, cancer or neoplasia, or a metastasis thereof. Such methods can be used to alternatively or additionally provide information on severity or progression of a tumor, cancer or neoplasia, or a metastasis thereof; prognosis of a tumor, cancer or neoplasia, or a metastasis thereof; and/or therapy or treatment of a tumor, cancer or neoplasia, or a metastasis thereof based upon detecting, diagnosing, screening or imaging.

As used herein, a "sufficient amount" or "effective amount" or an "amount sufficient" or an "amount effective" refers to an amount that is, in single or multiple doses, alone or in combination, with one or more other compositions, sufficient to bind to the receptor thereby detecting a hyperproliferative disorder (e.g., a tumor, cancer or neoplasia, or metastasis thereof). Thus, an amount sufficient or effective is that amount to allow diagnosis, screening, or imaging of a hyperproliferative disorder (e.g., a tumor, cancer or neoplasia, or metastasis thereof), identifying a subject that will respond to a therapy or treatment that targets a receptor (e.g., a hyperproliferative disorder such as a tumor, cancer or neoplasia, or metastasis thereof), or predicting therapeutic efficacy of a given treatment that targets a receptor, such as a hormone receptor, or that targets a hyperproliferative disorder (e.g., a tumor, cancer or neoplasia, or metastasis thereof).

Methods of detection, diagnostics or screening, such as in vitro, ex vivo, and vivo imaging methods, permit the detection of an agent. Such methods of detection include magnetic resonance spectroscopy (MRS), magnetic resonance imaging (MRI), positron-emission tomography (PET), gamma-scintigraphy, computed tomography (CT), Computed Axial Tomography (CAT), or single photon emission tomography (SPECT).

Methods also include detecting or diagnosing a subject having or at risk of having a tumor, cancer or neoplasia, (in vivo, ex vivo or in vitro). Such methods include contacting a biological sample from a subject with an agent under conditions whereby the agent can bind to a receptor or cell in the sample, and detecting the agent in the sample to ascertain the presence or absence or amount of a receptor or hyperproliferative disorder (e.g., a tumor, cancer or neoplasia, or metastasis thereof), in the sample, thereby detecting the hyperproliferative disorder (e.g., a tumor, cancer or neoplasia, or metastasis thereof), or screening for or diagnosing the subject as having or not having the hyperproliferative disorder (e.g., a tumor, cancer or neoplasia, or metastasis thereof), or imaging a hyperproliferative disorder (e.g., a tumor, cancer or neoplasia, or metastasis thereof).

For in vitro, ex vivo, and in vivo diagnosing, detecting, screening or imaging, the type of detection instrument available can depend upon a given label or conjugate. As an example, a radioisotope or paramagnetic isotope is suitable for in vivo detection, diagnosis, screening or imaging. The type of lable, such as a radionuclide or metal, will guide the selection of the instrument used. For instance, decay parameters of a chosen alpha, beta, or gamma radionuclide chosen can be detectable or measured by the selected instrument.

A "subject" refers to an animal, typically mammalian animals, such as but not limited to non-human primates (apes, gibbons, gorillas, chimpanzees, orangutans, macaques), domestic animals (dogs and cats), a farm animals (chickens, ducks, horses, cows, goats, sheep, pigs), experimental animal (mouse, rat, rabbit, guinea pig) and humans. Subjects include animal disease models, for example, animal models of undesirable or aberrant cell proliferation, such as a hyperproliferative disorder (e.g., a metastatic or non-metastatic tumor, cancer, malignancy or neoplasia) for analysis in vivo. Subjects include naturally occurring or non-naturally occurring mutated or non-human genetically engineered (e.g., transgenic or knockout) animals.

Subjects can be any age. For example, a subject (e.g., human) can be a newborn, infant, toddler, child, teenager, or an adult.

Subjects include those in need of a method of the invention, e.g., in need of diagnosis, detection, screening, imaging, or identifying or predicting. A subject is considered to be in need of a method of the invention where a method is likely to provide information concerning the presence or absence of, the extent or severity of, the location, the status or prognosis of, or possible treatment or therapy of a hyperproliferative disorder (e.g., a metastatic or non-metastatic tumor, cancer, malignancy or neoplasia).

Subjects appropriate for methods of the invention therefore include those having or at risk of having a hyperproliferative disorder (e.g., a tumor, cancer or neoplasia, or a metastasis thereof). At risk subjects include subjects that are at risk of developing a hyperproliferative disorder (e.g., a tumor, cancer or neoplasia, or a metastasis thereof), due to a genetic predispositon or family history, or environmental risk due to smoking, exposure to smoke or carcinogens, chemicals, sun exposure, etc. A subject may therefore be symptomatic or asymptomatic for a hyperproliferative disorder (e.g., a tumor, cancer or neoplasia, or a metastasis thereof). The invention methods are therefore applicable to a subject who is at risk of a hyperproliferative disorder (e.g., a tumor, cancer or neoplasia, or a metastasis thereof), but has not yet been diagnosed for a hyperproliferative disorder (e.g., a tumor, cancer or neoplasia, or a metastasis thereof).

Subjects appropriate for treatment include those having or at risk of having a metastatic or non-metastatic tumor, cancer, malignant or neoplastic cell, those undergoing as well as those who are undergoing or have undergone antiproliferative (e.g., metastatic or non-metastatic tumor, cancer, malignancy or neoplasia) therapy, including subjects where the tumor is in remission. "At risk" subjects typically have risk factors associated with undesirable or aberrant cell proliferation, development of hyperplasia (e.g., a tumor).

Particular examples of at risk or candidate subjects include those with cells that a receptor not typically expressed by normal cells, or at levels above normal. An agent can bind to such cells selectively, thereby revealing information on the size, severity, prognosis, location, and predicted treatment therapy and outcome. At risk subjects also include those that are candidates for and those that have undergone surgical resection, chemotherapy, immunotherapy, ionizing or chemical radiotherapy, local or regional thermal (hyperthermia) therapy. The invention is therefore applicable to treating a subject who is at risk of a metastatic or non-metastatic tumor, cancer, malignancy or neoplasia or a complication associated with a metastatic or non-metastatic tumor, cancer, malignancy or neoplasia, for example, due to metastatic or non-metastatic tumor, cancer, malignancy or neoplasia re-appearance or regrowth following a period of stability or remission.

Risk factors include gender, lifestyle (diet, smoking), occupation (medical and clinical personnel, agricultural and livestock workers), environmental factors (carcinogen exposure), family history (autoimmune disorders, diabetes, etc.), genetic predisposition, etc. For example, subjects at risk for developing melanoma include excess sun exposure (ultraviolet radiation), fair skin, high numbers of naevi (dysplastic nevus), patient phenotype, family history, or a history of a previous melanoma. Subjects at risk for developing cancer can therefore be identified by lifestyle, occupation, environmental factors, family history, and genetic screens for tumor associated genes, gene deletions or gene mutations. Subjects at risk for developing breast cancer lack Brcal , for example. Subjects at risk for developing colon cancer have early age or high frequency polyp formation, or deleted or mutated tumor suppressor genes, such as adenomatous polyposis coli (APC), for example.

Detectable agents can be incorporated into pharmaceutical compositions or formulations. Such pharmaceutical compositions/formulations are useful for administration to a subject, in vivo or ex vivo.

Pharmaceutical compositions and formulations include carriers or excipients for administration to a subject. As used herein the terms "pharmaceutically acceptable" and "physiologically acceptable" mean a biologically compatible formulation, gaseous, liquid or solid, or mixture thereof, which is suitable for one or more routes of administration, in vivo delivery or contact. A formulation is compatible in that it does not destroy activity of an active ingredient therein (e.g., a detectable agent), or induce adverse side effects that far outweigh any prophylactic or therapeutic effect or benefit.

Pharmaceutical compositions can optionally be formulated to be compatible with a particular mode or route of administration. Exemplary routes of administration include administration to a biological fluid or tissue, mucosal cell or tissue (e.g., mouth, buccal cavity, labia, nasopharynx, esophagus, trachea, lung, stomach, small intestine, vagina, rectum, or colon), neural cell or tissue (e.g., ganglia, motor or sensory neurons) or epithelial cell or tissue (e.g., nose, fingers, ears, cornea, conjunctiva, skin or dermis). Thus, pharmaceutical compositions include carriers (excipients, diluents, vehicles or filling agents) suitable for administration to any cell, tissue or organ, in vivo, ex vivo (e.g., tissue or organ transplant) or in vitro, by various routes and delivery, locally, regionally or systemically.

Detectable agents can be administered and methods may be practiced via systemic, regional or local administration, by any route. For example, an agent can be administered systemically, regionally or locally, intravenously, orally (e.g., ingestion or inhalation), intramuscularly, intraperitoneally, intradermally, subcutaneously, intracavity, intracranially, transdermally (topical), parenterally, e.g. transmucosally or rectally for detection. Agents and methods of the invention including pharmaceutical formulations can be administered via a (micro)encapsulated delivery system or packaged into an implant for administration.

Pharmaceutical formulations and delivery systems appropriate for the agents and methods of the invention are known in the art (see, e.g., *Remington: The Science and Practice of Pharmacy* (2003) $20t^h$ ed., Mack Publishing Co., Easton, Pa.; *Remington's Pharmaceutical Sciences* (1990) $18^{th}$ ed., Mack Publishing Co., Easton, Pa.; *The Merck Index* (1996) 12th ed., Merck Publishing Group, Whitehouse, N.J.; *Pharmaceutical Principles of Solid Dosage Forms* (1993), Technonic Publishing Co., Inc., Lancaster, Pa.; Ansel and Stoklosa, *Pharmaceutical Calculations* (2001) $11t^h$ ed., Lippincott Williams & Wilkins, Baltimore, Md.; and Poznansky et al., *Drug Delivery Systems* (1980), R. L. Juliano, ed., Oxford, N.Y., pp. 253-315).

Agents can be administered at any duration or frequency. Typically, an agent is administered as a bolus or is administered in multiple doses to provide detection, diagnosis, screening or imaging.

The invention provides kits including agents, combination compositions and pharmaceutical compositions/formulations thereof, packaged into a suitable packaging material. In one embodiment, a kit includes packaging material, an agent and instructions. In various aspects, the instructions are for administering to a subject or contact of the agent with a sample to diagnose, detect, screen or image a hyperproliferative disorder (e.g., a tumor, cancer or neoplasia, or a metastasis thereof).

The term "packaging material" refers to a physical structure housing one or more components of the kit. The packaging material can maintain the components sterilely, and can be made of material commonly used for such purposes (e.g., paper, corrugated fiber, glass, plastic, foil, ampules, vials, tubes, etc.). A kit can contain a plurality of components, e.g., two or more agents alone or in combination.

A kit optionally includes a label or insert including a description of the components (type, amounts, doses, etc.), instructions for use in vitro, in vivo, or ex vivo, and any other components therein. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., hard disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics and pharmacodynamics Labels or inserts can include information identifying manufacturer, lot numbers, manufacturer location and date, expiration dates.

Labels or inserts can include information on a hyperproliferative disorder (e.g., a tumor, cancer or neoplasia, or a metastasis thereof) for which a kit component may be used. Labels or inserts can include instructions for a clinician or subject for using one or more of the kit components in a method, diagnostic, detection, screening, indentification, or prediction protocol or regimen, including the methods of the invention. Instructions can include amounts of compound, frequency or duration of administration, and instructions for practicing any of the methods described herein. Kits therefore can additionally include labels or instructions for practicing any of the methods of the invention described herein including detection, diagnosis, screening, imaging or other methods.

Invention kits can additionally include a buffering agent, or a preservative or a stabilizing agent in a formulation containing an agent of the invention. Each component of the kit can be enclosed within an individual container and all of the various containers can be within a single package. Invention kits can be designed for cold storage.

Unless otherwise defined, all technical and scientific terms used herein have the same meaning as commonly understood by one of ordinary skill in the art to which this invention belongs. Although methods and materials similar or equivalent to those described herein can be used in the practice or study of the present invention, suitable methods and materials are described herein.

All of the features disclosed herein may be combined in any combination. Each feature disclosed in the specification may be replaced by an alternative feature serving a same, equivalent, or similar purpose. Thus, unless expressly stated otherwise, disclosed features (e.g., compound structures) are an example of a genus of equivalent or similar features.

All applications, publications, patents and other references, GenBank citations and ATCC citations cited herein are incorporated by reference in their entirety. In case of conflict, the specification, including definitions, will control.

As used herein, the singular forms "a", "and," and "the" include plural referents unless the context clearly indicates otherwise. Thus, for example, reference to an "agent," "compound" or "a receptor" includes a plurality of agents/compounds/receptors and reference to a "tumor," "cancer," "neoplasia" or "metastasis" thereof can include reference to one tumors, cancers, neoplasias, metastases, and so forth.

As used herein, all numerical values or numerical ranges include integers within such ranges and fractions of the values or the integers within ranges unless the context clearly indicates otherwise. Thus, to illustrate, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. Reference to a range of 0-72 hrs, includes 1, 2, 3, 4, 5, 6, 7 hrs, etc., as well as 1, 2, 3, 4, 5, 6, 7 minutes, etc., and so forth. Reference to a range of 0-72 hrs, includes 1, 2, 3, 4, 5, 6, 7 hrs, etc., as well as 1, 2, 3, 4, 5, 6, 7 minutes, etc., and so forth. Reference to a range of doses, such as 0.1-1 ug/kg, 1-10 ug/kg, 10-25 ug/kg, 25-50 ug/kg, 50-100 ug/kg,100-500 ug/kg, 500-1,000 ug/kg, 1-5 mg/kg, 5-10 mg/kg, 10-20 mg/kg, 20-50 mg/kg, 50-100 mg/kg, 100-250 mg/kg, 250-500 mg/kg, includes 0.11-0.9 ug/kg, 2-9 ug/kg, 11.5-24.5 ug/kg, 26-49 ug/kg, 55-90 ug/kg,125-400 ug/kg, 750-800 ug/kg, 1.1-4.9 mg/kg, 6-9 mg/kg, 11.5-19.5 mg/kg, 21-49 mg/kg, 55-90 mg/kg, 125-200 mg/kg, 275.5-450.1 mg/kg, etc. A series of ranges, for example, 1-10 ug/kg, 10-25 ug/kg, 25-50 ug/kg, 50-100 ug/kg,100-500 ug/kg, 500-1,000 ug/kg, 1-5 mg/kg, 5-10 mg/kg, 10-20 mg/kg, 20-50 mg/kg, 50-100 mg/kg, 100-250 mg/kg, 250-500 mg/kg, includes 1-25 ug/kg, 10-25 ug/kg, 25-100 ug/kg,100-1,000 ug/kg, 1-10 mg/kg, 1-20 mg/kg etc.

The invention is generally disclosed herein using affirmative language to describe the numerous embodiments. The invention also includes embodiments in which subject matter is excluded, in full or in part, such as substances or materials, method steps and conditions, protocols, or procedures. Thus, even though the invention is generally not expressed herein in terms of what the invention does not include aspects that are not expressly excluded in the invention are nevertheless disclosed herein.

A number of embodiments of the invention have been described. Nevertheless, one skilled in the art, without departing from the spirit and scope of the invention, can make various changes and modifications of the invention to adapt it to various usages and conditions. For example, salts, isomers, racemers, multimers of agents disclosed herein are within the scope of this invention. Accordingly, the following examples are intended to illustrate but not limit the scope of the invention claimed.

EXAMPLES

Example 1

This example includes methods used to determine LHRH- and LH receptor status in tumor biopsies.

LHRH Receptor Determination

The presence of LHRH receptor was determined in tumor biopsies from patients diagnosed with specific forms of cancer. In particular, cases of breast cancer, endometrial cancer and ovarian cancer diagnosed and analyzed included patients who were evaluated in the past for eligibility for Herceptin therapy. A database was established including age of the patient, TNM/FIGO staging information, estrogen, progesterone and HER2/neu receptor status for breast cancer cases, recurrence and survival information. Cases were reviewed for eligibility based on enough tumor available for analysis. Identifiers were removed from the tissue blocks and were given protocol identification numbers.

The Sequence Listing submitted herewith on compact disc is incorporated herein by reference.

Immunoperoxidase staining was performed on the tumor biopsy tissue using the GnRH(LHRH) receptor mouse monoclonal antibody stain (Clone A9E4) marketed by Vector Laboratories(VP-G811,Lot number 13308, Burlingame, Calif.) at a dilution of 1:30, and the Ventana NIEW DAB Detection kit. The immunoperoxidase stains were performed on one of the Ventana XT, Ventana Benchmark or Ventana Nexus units (Ventana Medical Systems,Inc. Tucson, Ariz.). The immunoperoxidase staining was analyzed utilizing the Ventana Image Analysis System, an adjunctive computer-assisted image analysis system functionally connected to an interactive microscope (Axio Imager, Carl Zeiss, NY). The quantitative analysis was performed utilizing the program for quantitation of the HER2/neu receptor which includes morphometric and colorimetric analysis.

Receptor status results were reported as 0, 1+, 2+ or 3+. In addition, a manual assessment of staining was performed using the following criteria: Non-immunoreactive; Immunoreactive, Score 1+: 1-25% positive cells; Immunoreactive, Score 2+: 26-50% positive cells; Immunoreactive, Score 3+: 51-75% positive cells; Immunoreactive, Score 4+: 76-100% positive cells. Assessment of strength of staining was added to the manual evaluation using the following criteria: 0: Negative; 1: Weak, only visible at high magnification; 2: Moderate staining visible at low magnification; 3: Strong staining visible at low magnification. The IHC figures list 0, +1, +2, or +3 as the particular score, which reflects the relative immunoreactive receptor present.

LH Receptor Determination

The presence of LH receptor was determined in tumor biopsies from patients diagnosed with specific forms of cancer (as described above). Immunoperoxidase staining of tumor biopsy tissues was performed using the rabbit anti-human polyclonal antibody targeting the C-terminal domain, (MBL Laboratories, Woburn Mass.), diluted at 1:30 and the Ventana NIEW DAB Detection kit. The immunoperoxidase stains were performed on one of the Ventana XT, Ventana Benchmark or Ventana Nexus units (Ventana Medical Systems, Inc. Tucson, Ariz.). The immunoperoxidase staining was analyzed utilizing the Ventana Image Analysis System, an adjunctive computer-assisted image analysis system functionally connected to an interactive microscope (Axio Imager, Carl Zeiss, NY). The quantitative analysis was performed utilizing the program for quantitation of the HER2/neu receptor which includes morphometric and colorimetric analysis.

Receptor status results were reported as 0, 1+, 2+ or 3+. In addition, a manual assessment of staining was performed using the following criteria: Non-immunoreactive; Immunoreactive, Score 1+: 1-25% positive cells; Immunoreactive, Score 2+: 26-50% positive cells; Immunoreactive, Score 3+: 51-75% positive cells; and, Immunoreactive, Score 4+: 76-100% positive cells. Assessment of strength of staining was added to the manual evaluation using the following criteria: 0: Negative; 1: Weak, only visible at high magnification; 2: Moderate staining visible at low magnification; and, 3: Strong staining visible at low magnification.

Example 2

This example includes receptor expression profiles of various human tumors.

Analysis of ovarian, endometrial and breast cancer tumors was performed according to the methods of Example 1.

Receptor Expression Profile in Ovarian Cancers

Receptor profiles were determined in 50 samples of ovarian cancer based upon the analysis of tissues from biopsies of primary tumors (1° biopsy), and recurrences. Of the 50 biopsies studied, 82% were positive for LHRH receptors. In particular, 54-56% graded immunoreactive with a score 1+, 26-28% graded 2-3+ staining for LHRH receptors, and, 18% graded non-immunoreactive for LHRH receptors with a score of 0. Analysis of the tumor biopsies for LH receptors revealed that, 98% were found to be positive for LH receptors. In particular, 40-44% graded immunoreactive with a score of 1+, 74% graded 2-3+, for LH-receptors, and, 2% graded non-immunoreactive with a score of 0. LH- and LHRH receptor profiles were also determined in 11 cases of ovarian cancers from biopsies of recurrent tumors. Of these 11 cases, 54.5% graded immunoreactive with a score of 1+, 27.2% graded 2+, and 9% graded 3+ for LHRH receptors. Analysis of the biopsies of recurrent tumors for LH receptors revealed that, 27% graded immunoreactive with a score of 1+, 54.5% graded 2+, and 18.1% graded 3+ for LH.

Receptor Expression Profile in Endometrial Cancers

Receptor profiles were determined in 50 samples of endometrial cancer representing 40 1° biopsies and 10 metastases. Of the 50 cases studied, 80-86% of the biopsies were positive for LHRH receptors. In particular, 50-66% graded immunoreactive with a score of 1+, 14-36% graded 2-3+, for LHRH receptors, and, 14-20% graded non-immunoreactive with a score of 0. Analysis of the biopsies for LH receptors revealed that , 96-98% were positive for LH receptors. In particular, 28-32% graded immunoreactive with a score of 1+, 64-70% graded 2-3+, for LH receptors, and 2-4% graded non-immunoreactive with a score of 0. LH- and LHRH receptor profiles were also determined in 10 cases of endometrial cancers from biopsies of metastases. Of these 10 cases, 40% graded immunoreactive with a score of 1+, 40% graded 2+, and 10% graded 3+ for LHRH receptors.

Analysis of the biopsies of metastases for LH receptors revealed that, 10% graded immunoreactive with a score of 1+, 30% graded 2+, and 30% graded 3+ for LH receptors.

Receptor Expression Profile in Breast Cancers

Receptor profiles were determined in 98 samples of breast cancer biopsies (primary, metastatic and recurrent) Of the 98 biopsies studied, 84-87% were positive for LHRH receptors. In particular, 48-57% graded immunreactive with a score of 1+, 26-38% graded 2-3+, and 13-26% were negative (0) for LHRH receptors. Analysis of biopsies for LH receptors, revealed that 99% were positive for LH receptors. In particular, 18-23% graded immunoreactive with a score of 1+, 74% graded 2-3+ and 1% showed negative staining for LHreceptors. In particular, LH- and LHRH receptor profiles were determined in 22 cases of breast cancer by analysis of tissues taken from biopsies of secondary (2°) or metastatic tumors. Of the 22 cases studied, 10% of the biopsies were positive for the LHRH receptor. In particular, 60% graded immunoreactive with a score of 1+, 13% graded 2+, and 15% graded 3+ for LHRH receptors in recurrences. Upon analysis of the biopsies for LH receptors, 95% were positive for LH receptor. In particular, 26.3% graded immunoreactive with a score of 1+, 47.3% graded 2+, and 31.5% graded 3+ for LH receptors in metastases.

In sum, the foregoing studies reveal that various human cancer tumors express LHRH- and LH receptors at high levels. In particular, LHRH- and LH receptors were expressed at high levels in ovarian, endometrial and breast tumors including metastases and recurrent tumors. Studies reveal that LHRH- and LH receptor expression is not compromised following standard of care treatment. Analysis of metastatic or secondary (2°) tumor biopsies revealed that recurrent tumors express both LHRH- and LH receptors. Furthermore, receptors can be expressed at higher levels in secondary (2°) tumors compared to levels expressed in primary tumors. For example, LHRH receptors have a greater level of expression in metastatic or secondary (2°) breast cancer tumors than in primary breast tumors.

Example 3

This example includes a determination of LHRH- and LH receptor status in various human tumor cell lines.

Quantification of Functional LHRH Receptors in Various Cancer Cell Lines

LHRH receptor presence has been reported for a number of human cancer cell lines using immunohistochemistry techniques as well as gene expression. However, these reports vary even within the same cell line because of differences in passage numbers of the cell line studied, and are therefore inconsistent. To detect and quantify the LHRH receptor status in human cancer cell lines, procedures and sensitivity of an array of cell lines were evaluated and quantified for functional LHRH receptors using immunohistochemistry techniques. The data were then correlated with sensitivity to EP-100 (KFAKFAKKFAKFAKK-FAKQHWSYGLRPG) (SEQ ID NO.: 1) treatment.

LHRH receptor status was determined using an array of human cancer cell lines. Cell cultures were obtained from the American Culture type and Tissue Collection and cultured according to standard conditions described by ATCC. Cell were seeded at a number of 10,000 cells/well into each well of glass chamber slide in 4 chamberslide compartments and cultivated in growth medial until confluent. Monolayers were fixed using 10% phosphate buffered formalin and preserved in ethanol after successive dehydration. These chamber slides underwent immunoperoxidase staining using the mouse monoclonal antibody for LHRH receptors (GNRH03, #MS-1139-P, LabVision). The immunoperoxidase procedure was performed on Ventana XT, Ventana Benchmark or Ventana Nexes Units.

Quantitative immunoperoxidase image analysis was conducted with the Ventana Image Analysis System (VIAS) adjunctive computer assisted image analysis system functionally connected to an interactive microscope (Axio Imager). The quantitative analysis was conducted with the program for quantification of Her2/neu receptor that included morphometric and colorimetric analysis. Receptor status results were reported as percentage of cells showing positive staining of the LHRH receptors under the following criteria: 0 non-immunoreactive, 1+: 1-25% positive, 2+26–50% positive, 3+51–75% positive cells. These data were compared to manual assessments of staining strength. The following cell lines were analyzed: MDA-MB-435S (p250) (estrogen receptor negative), T47 D (p 100) estrogen receptor alpha positive, MCF-7 (p 152) estrogen receptor alpha positive, MCF-10 A (p 100), PC-3 (p 26) androgen receptor negative, Kle (p 2), Hec-1A (p 10) and 3T3 (p 122), OVCAR-3 (p41) and SKOV-3 (p 40).

The data show that LHRH receptor negative ovarian cancer cell line SKOV-3 had a VIAS score of (0), and the ovarian cancer cell line OVCAR-3 scored (2+). Among breast cancer cell lines T47 D was (1+), MCF-7 (3+), MDA-MB-435S (3+), prostate cancer cell line, PC-3 (2+), endometrial cancer cell lines Kle (0) and Hec 1A (0). Non cancerous cell lines were represented by MCF-10 A breast epithelial (0) and 3T3 mouse fibroblast cells (0). Thus, various cancer cell lines present surface LHRH receptors to varying degrees.

Correlation of In Vitro Cytotoxicity of EP-100 in Human Cancer Cell Lines with Surface LHRH-Receptor Expression Levels Studies were designed to test receptor specificity, correlation of sensitivity to LHRH receptor expression and initial efficacy kinetics in vitro by comparing targeted kinetics to untargeted kinetics. The cytotoxicity of EP-100 (KFAK-FAKKFAKFAKKFAKQHWSYGLRPG) (SEQ ID NO.: 1) in human cancer cell lines expressing various degrees of LHRH receptors was determined in an array of studies ranging from incubations of 24 hours. Cytotoxicity was evaluated as $IC_{50}$ value for each cell line. The data were then correlated to LHRH receptor expression determined in the same culture through immunohistochemistry surface LHRH receptor staining as VIAS scores to determine specificity of EP-100 targeting.

In vitro toxicity of EP100 was analyzed in human cancer cell lines that over-express LHRH receptors at various receptor capacities (MDA-MB-4355 (575 fmol/mg protein (Chatzistamou et al., *Clinical Cancer Res.* 6:4158 (2000)), VIAS Score +3), MCF-7 (579 fmol/mg protein; VIAS Score 3+) T47 D (VIAS Score 1+), OVCAR-3 (196 fmol/mg protein (Volker et al., *American J Obstetrics and Gynecology* 186:171 (2002)), VIAS Score 2+), LNCaP (355 fmol/mg protein) PC-3 (197 fmol/mg protein, Leuschner et al. *The Prostate* 56:239 (2003), VIAS Score 2+), AN3-CA (IHC positive), Hec-1A (54 fmol/mg protein, VIAS score 0 (Volker et al., *American J Obstetrics and Gynecology* 186: 171 (2002), Chatzaki et al. *Cancer Res.* 56:2059 (1996)) among those two multi-drug resistant cancer cell lines. The LHRH-receptor negative cell lines SKOV-3 (VIAS Score 0) and Hec 1A were used as measure for specificity (Westphalen et al., *International J. Oncology* 17:1063 (2000)).

Cell cultures were prepared in 96 well plates using 10,000 cells/well and were allowed to attach for 48 hours. EP-100 in lyophilized form was freshly dissolved in saline and added into the multi-well plates at increasing concentrations of 0, 0.001, 0.01, 0.1, 1, 2, 5, 10 and 100 µM. Incubations were conducted for 24 h at 37° C. Cell viability was determined using formazan conversion assays (MTT assays). Controls contained USP saline or 0.1% TritonX-100™ as reference for 0 and 100% cell death, respectively.

Data were processed and analyzed using Graph Pad Prizm 4™ software (Graph Pad Prizm, Inc). Statistical analysis for significance was determined by a two-tailed Student's T-test.

Figure 2A:
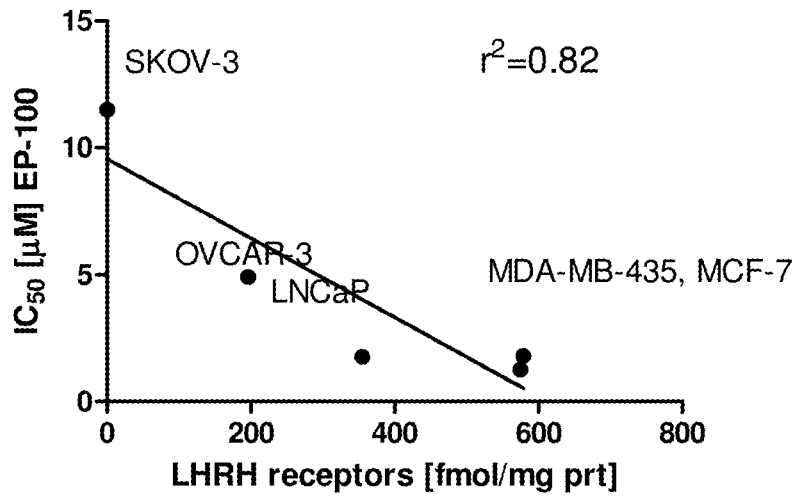
FIGS. 2A and 2B: Human cancer cell lines show high correlation to sensitivity to EP-100 (KFAKFAKKFAKFAKKFAKQHWSYGLRPG) (SEQ ID NO.:1) and their presence levels of functional LHRH receptors determined as receptor capacities and VIAS Scores. Human cancer cell lines were incubated with EP-100 for 24 h showed variable sensitivities to the drug, which correlated with LHRH receptor capacities among those two multi-drug resistant cells.
Figure 2B:
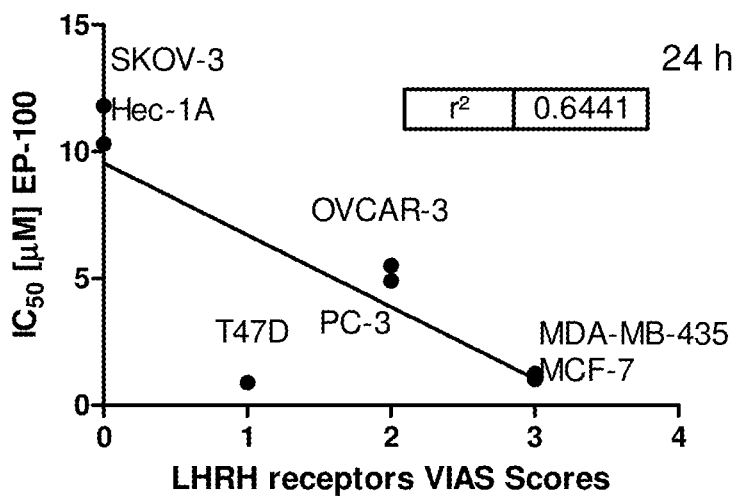

Human cancer cell lines showed variable sensitivities to the drug, which correlated with LHRH receptor capacities. Human breast cancer cell line (MDA-MB-231, negative for estrogen receptors, Her2/neu and progesterone receptors, multi drug resistant) was insensitive to cisplatinum, but sensitive to EP-100 (5.5 µM), followed by the human endometrial cancer cell line AN3-CA (3.3 µM), the ovarian cancer cell line OVCAR-3 (3.0 µM), the prostate cancer cell lines LNCaP (1.5 µM) and PC-3 (5.5 µM). The MDA-MB-4355 breast cancer cell line showed highest sensitivity with 0.8 µM and has the highest LHRH receptor capacity of all tested cell lines (FIGS. 2A and 2B). SKOV-3, a LHRH receptor negative ovarian cancer cell line, was insensitive to EP-100 with>10 µM.

In conclusion, human cancer cell lines show high correlation of sensitivity to EP-100 and their surface LHRH receptor expression determined as LHRH receptor capacities ($r^2$=0.82) as well as LHRH receptor expression determined and quantified in immunohistochemistry methods ($r^2$=0.64). The greater LHRH receptor expression on the cell surface correlates with increased sensitivity to LHRH receptor targeting drug EP-100.

Example 4

This example includes determination and quantification of LH-Receptors and LHRH-Receptors in human cancer cell lines through LHRH receptor and LH/hCG receptor gene expression assays.

A quantitative human LHRH receptor and LH/hCG receptor gene expression assay has been developed to identify malignant cell lines and patient tumor specimens. LHRH receptor and LH/hCG receptor mRNA levels in multiple cancer cell lines were measured to identify potential targets for LHRH- and LH/CG receptors. This method determines the LHRH- and LH/CG receptor expression on RNA detection levels.

In brief, RNA was isolated from cell cultures or tissue samples using the RNeasy Mini Kit (Qiagen #74104) according to the standard protocol provided. Contaminating genomic DNA was removed through an on column DNase digestion step. RNA samples were stored in RNase-free water containing RNase inhibitor at −80° C. until analysis.

For each RNA type quantification, reverse transcriptase polymerase chain reaction was conducted using Taqman primers for LHRH receptor and LH receptor. The LH receptor Set 2 primer/probe was designed to amplify full length transcripts containing the transmembrane region of the LH receptor. RNA was quantified and analyzed for integrity and DNA contamination using the Agilent 2100 Bioanalyzer, according to manufacturer instructions. Profiles generated by the Agilent provide concentration, visual inspection of RNA integrity, and an RNA integrity number based on the entire electrophoretic trace of a sample.

What is claimed:

1. A method of analyzing a pancreatic, hepatic, melanoma, kidney, gastrointestinal, lung, lymphoma or leukemia sample, the method comprising:
   (a) contacting the pancreatic, hepatic, melanoma, kidney, gastrointestinal, lung, lymphoma or leukemia sample from a subject, with a hormone polypeptide or hormone polypeptide analog that binds to LHRH- or hCG/LH receptors under conditions allowing the hormone or hormone analog to bind the LHRH- or hCG/LH receptors;
   (b) determining an amount of LHRH- or hCG/LH receptors in the sample by detecting the amount of hormone polypeptide or hormone polypeptide analog that is bound to the LHRH- or hCG/LH receptors in the sample;
   (c) contacting cells obtained from the sample with a peptide comprising the cytotoxic sequence KFAKFAKKFAKFAKKFAKQHWSYGLRPG (SEQ ID NO: 1); and
   (d) after the contacting of (c), determining the IC50 value according to a sensitivity of the cells to SEQ ID NO:1, wherein the IC50 value is 5.5 μM or less and wherein greater LHRH- or hCG/LH receptor expression indicates increased sensitivity of the cells.

2. The method of claim 1, comprising identifying a sample according to the determining of (b), wherein greater than 50% of the cells express LHRH- or hCG/LH receptors.

3. The method of claim 1, wherein the cytotoxic sequence is biotin-conjugated or fluorescein conjugated.

4. The method of claim 1, wherein the hormone polypeptide or hormone polypeptide analog comprises one or more D-amino acids.

5. The method of claim 1, wherein the hormone polypeptide or hormone polypeptide analog is biotin-conjugated or fluorescein-conjugated.

6. The method of claim 1, wherein (a) comprises contacting the pancreatic sample from the subject with the hormone polypeptide or the hormone polypeptide analog that binds to LHRH- or hCG/LH receptors under conditions allowing the hormone or hormone analog to bind the LHRH- or hCG/LH receptors.

7. The method of claim 1, wherein (a) comprises contacting the hepatic sample from the subject with the hormone polypeptide or the hormone polypeptide analog that binds to LHRH- or hCG/LH receptors under conditions allowing the hormone or hormone analog to bind the LHRH- or hCG/LH receptors.

8. The method of claim 1, wherein (a) comprises contacting the melanoma sample from the subject with the hormone polypeptide or the hormone polypeptide analog that binds to LHRH- or hCG/LH receptors under conditions allowing the hormone or hormone analog to bind the LHRH- or hCG/LH receptors.

9. The method of claim 8, wherein the melanoma sample comprises a melanoma of the eye sample.

10. The method of claim 9, wherein the melanoma sample comprises a melanoma of the skin sample.

11. The method of claim 1, wherein (a) comprises contacting the kidney sample from the subject with the hormone polypeptide or the hormone polypeptide analog that binds to LHRH- or hCG/LH receptors under conditions allowing the hormone or hormone analog to bind the LHRH- or hCG/LH receptors.

12. The method of claim 1, wherein (a) comprises contacting the gastrointestinal sample from the subject with the hormone polypeptide or the hormone polypeptide analog that binds to LHRH- or hCG/LH receptors under conditions allowing the hormone or hormone analog to bind the LHRH- or hCG/LH receptors.

13. The method of claim 12, wherein the gastrointestinal sample comprises a colon sample.

14. The method of claim 1, wherein (a) comprises contacting the lung sample from the subject with the hormone polypeptide or the hormone polypeptide analog that binds to LHRH- or hCG/LH receptors under conditions allowing the hormone or hormone analog to bind the LHRH- or hCG/LH receptors.

15. The method of claim 1, wherein (a) comprises contacting the lymphoma sample from the subject with the hormone polypeptide or the hormone polypeptide analog that binds to LHRH- or hCG/LH receptors under conditions allowing the hormone or hormone analog to bind the LHRH- or hCG/LH receptors.

16. The method of claim 15, wherein the lymphoma sample comprises a non-Hodgkin's lymphoma sample.

17. The method of claim 1, wherein (a) comprises contacting the leukemia sample from the subject with the hormone polypeptide or the hormone polypeptide analog that binds to LHRH- or hCG/LH receptors under conditions allowing the hormone or hormone analog to bind the LHRH- or hCG/LH receptors.

18. The method of claim 1, comprising identifying a sample according to the determining of (b), wherein between 10 and 90% of the cells express LHRH- or hCG/LH receptors.

* * * * *